US011179444B2

(12) United States Patent
Stowell et al.

(10) Patent No.: US 11,179,444 B2
(45) Date of Patent: Nov. 23, 2021

(54) GLUCAGON ANALOGS AND METHODS OF USE THEREOF

(71) Applicant: AMIDEBIO, LLC, Boulder, CO (US)

(72) Inventors: Michael H. B. Stowell, Boulder, CO (US); Mikhail Plam, Boulder, CO (US); Yanyu Peng, Superior, CO (US)

(73) Assignee: AmideBio, LLC, Louisville, CO (US)

(*) Notice: Subject to any disclaimer, the term of this patent is extended or adjusted under 35 U.S.C. 154(b) by 0 days.

(21) Appl. No.: 16/307,905

(22) PCT Filed: Jun. 9, 2017

(86) PCT No.: PCT/US2017/036808
§ 371 (c)(1),
(2) Date: Dec. 6, 2018

(87) PCT Pub. No.: WO2017/214543
PCT Pub. Date: Dec. 14, 2017

(65) Prior Publication Data
US 2019/0298805 A1    Oct. 3, 2019

Related U.S. Application Data

(60) Provisional application No. 62/348,101, filed on Jun. 9, 2016.

(51) Int. Cl.
*A61K 38/26*     (2006.01)
*A61P 5/48*      (2006.01)
*A61P 3/08*      (2006.01)
*A61K 9/00*      (2006.01)
*C12N 15/81*     (2006.01)
*A61K 35/37*     (2015.01)
*C07K 14/605*    (2006.01)
*A61K 35/76*     (2015.01)

(52) U.S. Cl.
CPC ............ *A61K 38/26* (2013.01); *A61K 9/0019* (2013.01); *A61K 35/37* (2013.01); *A61K 35/76* (2013.01); *A61P 3/08* (2018.01); *A61P 5/48* (2018.01); *C07K 14/605* (2013.01); *C12N 15/81* (2013.01); *C07K 2319/00* (2013.01); *Y02A 50/30* (2018.01)

(58) Field of Classification Search
None
See application file for complete search history.

(56) References Cited

U.S. PATENT DOCUMENTS

| | | |
|---|---|---|
| 4,507,230 A | 3/1985 | Tam et al. |
| 7,994,122 B2 | 8/2011 | Riber et al. |
| 8,642,541 B2 | 2/2014 | Meier et al. |
| 8,642,727 B2 | 2/2014 | Larsen et al. |
| 2010/0190699 A1 | 7/2010 | Dimarchi et al. |
| 2012/0028890 A1 | 2/2012 | Nistor et al. |
| 2013/0053310 A1 | 2/2013 | Lau et al. |
| 2013/0157935 A1 | 6/2013 | Meier et al. |
| 2013/0157953 A1 | 6/2013 | Petersen et al. |
| 2013/0316941 A1 | 11/2013 | Hamprecht et al. |

FOREIGN PATENT DOCUMENTS

| | | | |
|---|---|---|---|
| CN | 101985470 A | 3/2011 | |
| CN | 102134274 A | 7/2011 | |
| CN | 102292347 A | 12/2011 | |
| CN | 102933598 A | 2/2013 | |
| CN | 104812772 A | 7/2015 | |
| CN | 104961822 A | 10/2015 | |
| CN | 105396126 A | 3/2016 | |
| CN | 106084031 A | 11/2016 | |
| WO | WO-9405699 A1 | 3/1994 | |
| WO | WO-2010071807 A1 | 6/2010 | |
| WO | WO-2011117417 A1 * | 9/2011 | ............... A61P 9/00 |
| WO | WO-2013098408 A1 | 7/2013 | |
| WO | WO-2015081440 A1 | 6/2015 | |
| WO | WO-2017182873 A2 | 10/2017 | |
| WO | WO-2017214543 A1 | 12/2017 | |

OTHER PUBLICATIONS

Conchillo-Solé et al. AGGRESCAN: a server for the prediction and evaluation of "hot spots" of aggregation in polypeptides. BMC Bioinformatics 8:65 (Feb. 27, 2007). 17 pages.
Lennick, et al. High-level expression of alpha-human atrial natriuretic peptide from multiple joined genes in *Escherichia coli*. Gene. 1987;61(1):103-12.
PCT/US2017/036808 International Search Report and Written Opinion dated Aug. 21, 2017.
Pedersen et al. N- and C-Terminal Hydrophobic Patches Are Involved in Fibrillation of Glucagon. Biochemistry 45 (48):14503-14512 (Nov. 9, 2006).
Prévost et al. Identification of Key Residues for the Binding of Glucagon to the N-Terminal Domain of its Receptor: An Alanine Scan and Modeling Study. Horm Metab Res 44:804-809 (2012).
Unson. Molecular determinants of glucagon receptor signaling. Peptide Science 66(4):218-235 (2002).
Wang, et al. Expanding the genetic code for biological studies. Chem Biol. Mar. 27, 2009;16(3):323-36. doi: 10.1016/j.chembiol.2009.03.001.
Wang et al. Expanding the Genetic Code of *Escherichia coli*, Science 292:498-500 (Apr. 20, 2001).
EP17811105.0 Partial Supplementary European Search Report dated Feb. 14, 2020.

(Continued)

*Primary Examiner* — James H Alstrum-Acevedo
*Assistant Examiner* — Tara L Martinez
(74) *Attorney, Agent, or Firm* — Wilson Sonsini Goodrich & Rosati

(57) ABSTRACT

The subject matter of this invention is directed towards chemically and thermodynamically stable glucagon analogs that are resistant to deamidation and fibrillation. The invention further discloses improved methods for the recombinant expression and purification of glucagon analogs.

6 Claims, 7 Drawing Sheets

Specification includes a Sequence Listing.

(56) References Cited

OTHER PUBLICATIONS

Marqusee, S. and Baldwin, R.L. Helix stabilization by Glu-***Lys+ salt bridges in short peptides of de novo design. Proc. Natl Acad. Sci. USA, 84, 8898-8902 (1987).
EP17811105.0 Extended European Search Report dated Apr. 30, 2020.
Chabenne et al. A glucagon analog chemically stabilized for immediate treatment of lifethreatening hypoglycemia. Molecular Metabolism 3:293-300 (2014). Available online Jan. 22, 2014.
EP21163549.5 Extended European Search Report dated Aug. 12, 2021.
Joshi et al. The degradation pathways of glucagon in acidic solutions. International Journal of Pharmaceutics 203:115-125 (2000).
CN201780049092.4 Office Action and Search Report dated Oct. 8, 2021 (w/ partial English translation).

* cited by examiner

```
                        SEQUENCE LISTING

<160> NUMBER OF SEQ ID NOS: 30

<210> SEQ ID NO 1
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Glu Leu Ala Asn Thr
            20                  25

<210> SEQ ID NO 2
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

His Ser Gln Gly Thr Phe Thr Ser Asp Tyr Ser Lys Tyr Leu Asp Ser
1               5                   10                  15

Arg Arg Ala Gln Asp Phe Val Gln Lys Leu Ala Asn Thr
            20                  25

<210> SEQ ID NO 3
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

His Ser Gln Gly Thr Phe Thr Ser Asp Tyr Ser Lys Tyr Leu Asp Ser
1               5                   10                  15

Arg Arg Ala Gln Asp Phe Ala Gln Glu Leu Ala Asn Thr
            20                  25

<210> SEQ ID NO 4
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4
```

His Ser Gln Gly Thr Phe Thr Ser Asp Tyr Ser Lys Tyr Leu Asp Ser
1               5                   10                  15

Arg Arg Ala Gln Asp Phe Ala Gln Lys Leu Ala Asn Thr
            20                  25

<210> SEQ ID NO 5
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

His Ser Gln Gly Thr Phe Thr Ser Asp Tyr Ser Lys Tyr Leu Asp Ser
1               5                   10                  15

Arg Arg Ala Gln Asp Phe Val Gln Asp Leu Ala Asn Thr
            20                  25

<210> SEQ ID NO 6
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

His Ser Gln Gly Thr Phe Thr Ser Asp Tyr Ser Lys Tyr Leu Asp Ser
1               5                   10                  15

Arg Arg Ala Gln Asp Phe Val Gln His Leu Ala Asn Thr
            20                  25

<210> SEQ ID NO 7
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

His Ser Gln Gly Thr Phe Thr Ser Asp Tyr Ser Lys Tyr Leu Asp Ser
1               5                   10                  15

Arg Arg Ala Gln Asp Phe Val Gln Asp Leu Ala Asp Thr
            20                  25

<210> SEQ ID NO 8
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

His Ser Gln Gly Thr Phe Thr Ser Asp Tyr Ser Lys Tyr Leu Asp Ser
1               5                   10                  15

Arg Arg Ala Gln Asp Phe Val Gln Asp Leu Ala Glu Thr
            20                  25

<210> SEQ ID NO 9
<211> LENGTH: 29
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 9

His Ser Gln Gly Thr Phe Thr Ser Asp Tyr Ser Lys Tyr Leu Asp Ser
1               5                   10                  15

Arg Arg Ala Gln Asp Phe Val Gln Lys Leu Glu Asn Thr
            20                  25

<210> SEQ ID NO 10
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

His Ser Gln Gly Thr Phe Thr Ser Asp Tyr Ser Lys Tyr Leu Asp Ser
1               5                   10                  15

Arg Arg Ala Gln Asp Phe Val Glu Lys Leu Glu Asn Thr
            20                  25

<210> SEQ ID NO 11
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

His Ser Gln Gly Thr Phe Thr Ser Asp Tyr Ser Lys Tyr Leu Asp Ser
1               5                   10                  15

Arg Arg Ala Gln Asp Phe Val Glu Lys Leu Glu Ser Thr
            20                  25

<210> SEQ ID NO 12
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

His Ser Gln Gly Thr Phe Thr Ser Asp Tyr Ser Lys Tyr Leu Asp Ser
1               5                   10                  15

Arg Arg Ala Gln Asp Phe Val Gln Lys Leu Leu Asn Thr
            20                  25

<210> SEQ ID NO 13
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

His Ser Gln Gly Thr Phe Thr Ser Asp Tyr Ser Lys Tyr Leu Asp Ser
1               5                   10                  15

Arg Arg Ala Gln Asp Phe Val Gln Lys Leu Leu Ser Thr
```

20                  25

<210> SEQ ID NO 14
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

His Ser Gln Gly Thr Phe Thr Ser Asp Tyr Ser Lys Tyr Leu Asp Ser
1               5                   10                  15

Arg Arg Ala Gln Asp Phe Val Glu Lys Leu Leu Ser Thr
            20                  25

<210> SEQ ID NO 15
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

His Ser Gln Gly Thr Phe Thr Ser Asp Tyr Ser Lys Tyr Leu Asp Ser
1               5                   10                  15

Arg Arg Ala Gln Asp Phe Val Glu Lys Leu Glu Lys Thr
            20                  25

<210> SEQ ID NO 16
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

His Ser Gln Gly Thr Phe Thr Ser Asp Tyr Ser Lys Tyr Leu Asp Ser
1               5                   10                  15

Arg Arg Ala Gln Asp Phe Val Glu Lys Leu Ala Asn Thr
            20                  25

<210> SEQ ID NO 17
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

His Ser Gln Gly Thr Phe Thr Ser Asp Tyr Ser Lys Tyr Leu Asp Ser
1               5                   10                  15

Arg Arg Ala Gln Asp Phe Val Glu Lys Leu Ala Ser Thr
            20                  25

<210> SEQ ID NO 18
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 18

His Ser Gln Gly Thr Phe Thr Ser Asp Tyr Ser Lys Tyr Leu Asp Ser
1               5                   10                  15

Arg Arg Ala Gln Asp Phe Val Ala Lys Leu Ala Asn Thr
            20                  25

<210> SEQ ID NO 19
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

His Ser Gln Gly Thr Phe Thr Ser Asp Tyr Ser Lys Tyr Leu Asp Ser
1               5                   10                  15

Arg Arg Ala Gln Asp Phe Val Ala Lys Leu Ala Lys Thr
            20                  25

<210> SEQ ID NO 20
<211> LENGTH: 29
<212> TYPE: PRT
<213> ORGANISM: Unknown
<220> FEATURE:
<223> OTHER INFORMATION: Description of Unknown:
      Native glucagon sequence

<400> SEQUENCE: 20

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 21
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Lys Ala Ile Phe Val Leu Lys Gly Ser Leu Asp Arg Asp Pro Glu
1               5                   10                  15

Phe Pro Ser Asp Lys Pro His His Lys Lys His His Lys His His
            20                  25                  30

Ser Ser Gly Ser Leu Glu
        35

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(10)
<223> OTHER INFORMATION: This sequence may encompass 5-10 residues

<400> SEQUENCE: 22

Lys Lys Lys Lys Lys Lys Lys Lys Lys Lys
1               5                   10
```

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(10)
<223> OTHER INFORMATION: This sequence may encompass 5-10 residues

<400> SEQUENCE: 23

His His His His His His His His His His
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(10)
<223> OTHER INFORMATION: This sequence may encompass 5-10 residues

<400> SEQUENCE: 24

Glu Glu Glu Glu Glu Glu Glu Glu Glu Glu
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(10)
<223> OTHER INFORMATION: This sequence may encompass 5-10 residues

<400> SEQUENCE: 25

Arg Arg Arg Arg Arg Arg Arg Arg Arg Arg
1               5                   10

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 26

His His His His His His
1               5

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

```
Lys Lys Lys Lys Lys Lys
1               5

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Glu Glu Glu Glu Glu Glu
1               5

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Arg Arg Arg Arg Arg
1               5

<210> SEQ ID NO 30
<211> LENGTH: 22
<212> TYPE: PRT
<213> ORGANISM: Unknown
<220> FEATURE:
<223> OTHER INFORMATION: Description of Unknown:
      Insulin sequence

<400> SEQUENCE: 30

Phe Val Asn Gln His Leu Cys Gly Ser His Leu Val Glu Ala Leu Tyr
1               5                   10                  15

Leu Val Cys Gly Glu Arg
            20
```

GLUCAGON ANALOGS AND METHODS OF USE THEREOF

CROSS REFERENCE

This application is a U.S. National Phase Application under 35 U.S.C. § 371 of International Application No. PCT/US2017/036808, filed Jun. 9, 2017, which claims the benefit of U.S. Provisional Patent Application No. 62/348, 101, filed Jun. 9, 2016, the entire contents of which are incorporated by reference.

SEQUENCE LISTING

The instant application contains a Sequence Listing which has been submitted electronically in ASCII format and is hereby incorporated by reference in its entirety. Said ASCII copy, created on May 26, 2017, is named 39538-711_601_SL.txt and is 11,052 bytes in size

BACKGROUND

Congenital hyperinsulinism (CH) is a rare condition characterized by persistent hypoglycemia in children and newborns with an incidence of approximately 1/30,000 births in the United States. More than 60% of neonates with CH develop hypoglycemia during the first month and the remainder will be diagnosed within the first year or shortly thereafter. Of the different types of CH, diazoxide unresponsive severe-persistent CH needs to be treated using glucagon and/or combined glucose and glucagon. Additionally, there are over 20,000 hypoglycemic emergency hospital visits annually in the US and over 2,000 deaths, many of which are a result of failure to rapidly treat hypoglycemia in type I diabetics, and could be prevented by administration of glucagon.

SUMMARY

The present disclosure relates to compositions and methods of use for treatment of hypoglycemia. Described herein are compositions of glucagon analogs that are stable in solution at physiological pH. In some embodiments, a composition comprises a glucagon analog, wherein the glucagon analog consists of naturally occurring amino acids; and the glucagon analog is stable in solution at a pH between pH 6 and pH 8. In various aspects, the glucagon analog is stable in solution at a pH of about 7.4.

In some aspects, being stable in solution comprises being resistant to fibrillation, being resistant to chemical degradation, or a combination thereof. In other aspects, being resistant to fibrillation comprises having a decreased computed aggregation score aggregation compared to native glucagon and decreased experimental aggregation after a time period of at least 7 days in solution. In further aspects, the glucagon analog comprises a mutation in a region corresponding to an aggregration pronein native glucagon. In still further aspects, the amino acid residues Phe6, Tyr10, or Tyr13 of native glucagon, or a combination thereof, are replaced with another amino acid residue.

In various aspects, being resistant to chemical degradation comprises being thermodynamically stable, being chemically stable, or a combination thereof. In some aspects, the glucagon analog is thermodynamically stable when at least 80% of the glucagon analog is undegraded or unaggregated after at least 7 days in a solution. In other aspects, the glucagon analog is resistant to chemical degradation if deamidation of the glucagon analog is reduced after a time period of at least 7 days relative to native glucagon. In some aspects, the glucagon analog comprises at least one mutation in a region between amino acid residue 22 and amino acid residue 27. In further aspects, the glucagon analog comprising at least one mutation in a region between amino acid residue 22 and amino acid residue 27 has a computed aggregation score less than that of native glucagon. In still further aspects, the glucagon analog comprising at least one mutation in a region between amino acid residue 22 and amino acid residue 27 creates an α-helix stabilization.

In some aspects, the glucagon analog has at least 80%, 85%, 90%, 95%, 98%, or 99% sequence identity to any one of SEQ ID NO: 1-SEQ ID NO: 19, or a fragment thereof. In other aspects, the glucagon analog comprises any one of SEQ ID NO: 1-SEQ ID NO: 19. In further aspects, the glucagon analog is a human glucagon analog.

In various aspects, the glucagon analog is at least 90%, 95%, 97%, or 99% pure.

In additional aspects, the C-terminus of the glucagon analog comprises a stabilized α-helical structure of a C-terminus of native glucagon. In some aspects, the glucagon analog comprises Phe22, Val23, Trp25, Leu26, Met27, Asp15, or a combination thereof relative to native glucagon. In some aspects, the glucagon analog comprises mutations at Phe22, Val23, Trp25, Leu26, Met27, Asp15, or a combination thereof relative to native glucagon. In other aspects, the glucagon analog has at least 10%, 20%, 30%, 40%, 50%, 60%, 70%, 80%, or 90% glucagon receptor agonist activity of native glucagon.

In some aspects, the glucagon analog maintains at least 95% potency for at least 2 years when stored at 4° C.

In further aspects, the glucagon analog maintains at least 95% potency for at least 3 months when stored at 40° C.

In various embodiments, a pharmaceutical composition comprises any of the aforementioned aspects of the composition and a pharmaceutically acceptable diluent. In further aspects, the pharmaceutical composition is formulated for subcutaneous, intravenous, intraperitoneal, intramuscular, intra-arterial, or transdermal administration.

In some embodiments, a polynucleotide comprises a nucleic acid sequence that encodes the glucagon analog according to any one of the aforementioned compositions.

In other embodiments, a vector comprises a first nucleotide sequence encoding an expression tag; a second nucleotide sequence encoding a cleavage tag; and a third nucleotide sequence encoding the glucagon analog according to any one of aforementioned compositions wherein the first, second, and third nucleotide sequences are arranged in operable combination; wherein the expression tag comprises an amino acid sequence having at least 80% sequence identity to SEQ ID NO: 21 (MKAIFVLKGSLDRDPE-FPSDKPHHKKHHKKHHSSGSLE), and; wherein the cleavage tag comprises a Trp (W) amino acid. In some aspects, the expression tag further comprises an affinity tag. In other aspects, the affinity tag comprises at least six amino acids having charged side chains.

In some embodiments, the vector further comprises a nucleotide sequence encoding an inclusion-body directing peptide. In various aspects, the inclusion-body directing peptide is selected from the group consisting of: a ketosteroid isomerase, an inclusion-body directing functional fragment of a ketosteroid isomerase, an inclusion-body directing functional homolog of a ketosteroid isomerase, a BRCA2 peptide, an inclusion-body directing functional fragment of BRCA2, and an inclusion-body directing functional homolog of BRCA2.

In other embodiments, the vector further comprises a nucleotide promoter sequence which is active in a bacteria cell or a yeast cell.

In various embodiments, a method for producing a glucagon analog comprises expressing a heterologous fusion peptide in a genetically modified cell, the heterologous fusion peptide comprising an expression tag, a cleavage tag, and the glucagon analog of any one of the aforementioned compositions, wherein the expression tag comprises an amino acid sequence having at least 80% sequence identity to SEQ ID NO: 21 (MKAIFVLKGSLDRDPE-FPSDKPHHKKHHKKHHSSGSLE) or a fragment thereof, and wherein the cleavage tag comprises a Trp (W) amino acid; and cleaving the heterologous fusion peptide to release the glucagon analog from the heterologous fusion peptide, thereby producing the glucagon analog.

In some aspects, the glucagon analog is at least 95% pure. In other aspects, the glucagon analog is at least 99% pure. In various aspects, the expression tag further comprises an affinity tag. In further aspects, the affinity tag comprises at least six amino acids having charged side chains.

In other embodiments, the method further comprises binding the heterologous fusion peptide to an affinity material via the affinity tag. In some aspects, subsequent to binding the heterologous fusion peptide to the affinity material, the method further comprises washing the affinity material to remove unbound material. In various embodiments, cleaving the heterologous fusion peptide in the second part of the method occurs while the heterologous fusion peptide is bound to the affinity material via the affinity tag. In other aspects, subsequent to binding the heterologous fusion peptide to the affinity material, the method further comprises subjecting the heterologous fusion peptide to conditions sufficient to fold the target peptide.

In other aspects, the heterologous fusion peptide further comprises an inclusion-body directing peptide. In some aspects, the inclusion-body directing peptide is selected from the group consisting of: a ketosteroid isomerase, an inclusion-body directing functional fragment of a ketosteroid isomerase, an inclusion-body directing functional homolog of a ketosteroid isomerase, a BRCA2 peptide, an inclusion-body directing functional fragment of BRCA2, and an inclusion-body directing functional homolog of BRCA2.

In other aspects, prior to cleaving the heterologous fusion peptide, the method further comprises removing inclusion bodies containing the fusion peptide from the genetically modified cell and solubilizing the fusion peptide in the inclusion bodies. In some aspects, the cleaving of the second part of the method is performed with an agent selected from the group consisting of: NBS, NCS, and $Pd(H_2O)_4$.

In additional aspects, the heterologous fusion peptide is secreted from the genetically modified cell after it is expressed.

In various embodiments, the method further comprises lysing the genetically modified cell after the heterologous fusion peptide is expressed. In some aspects, the genetically modified cell is a bacterial cell. In other aspects, the bacterial cell is an *Escherichia coli* cell. In further aspects, the genetically modified cell is a yeast cell. In other aspects, the heterologous fusion peptide further comprises a secretion peptide for use in the yeast cell.

In other embodiments, a method of treating hypoglycemia in a patient in need thereof comprises administering the composition of any one of aforementioned embodiments or the pharmaceutical composition of any one of aforementioned embodiments to the patient. In some aspects, the patient has diabetes. In other aspects, the diabetes is type I diabetes. In further aspects, the diabetes is type II diabetes. In various aspects, the patient has congenital hyperinsulinism.

In some embodiments, the method comprises administering the glucagon analog by injection, a patch, or a pump. In other aspects, the injection is a subcutaneous, intravenous, intraperitoneal, intramuscular, intra-arterial, or transdermal injection. In further aspects, the pump is a closed loop pump system.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
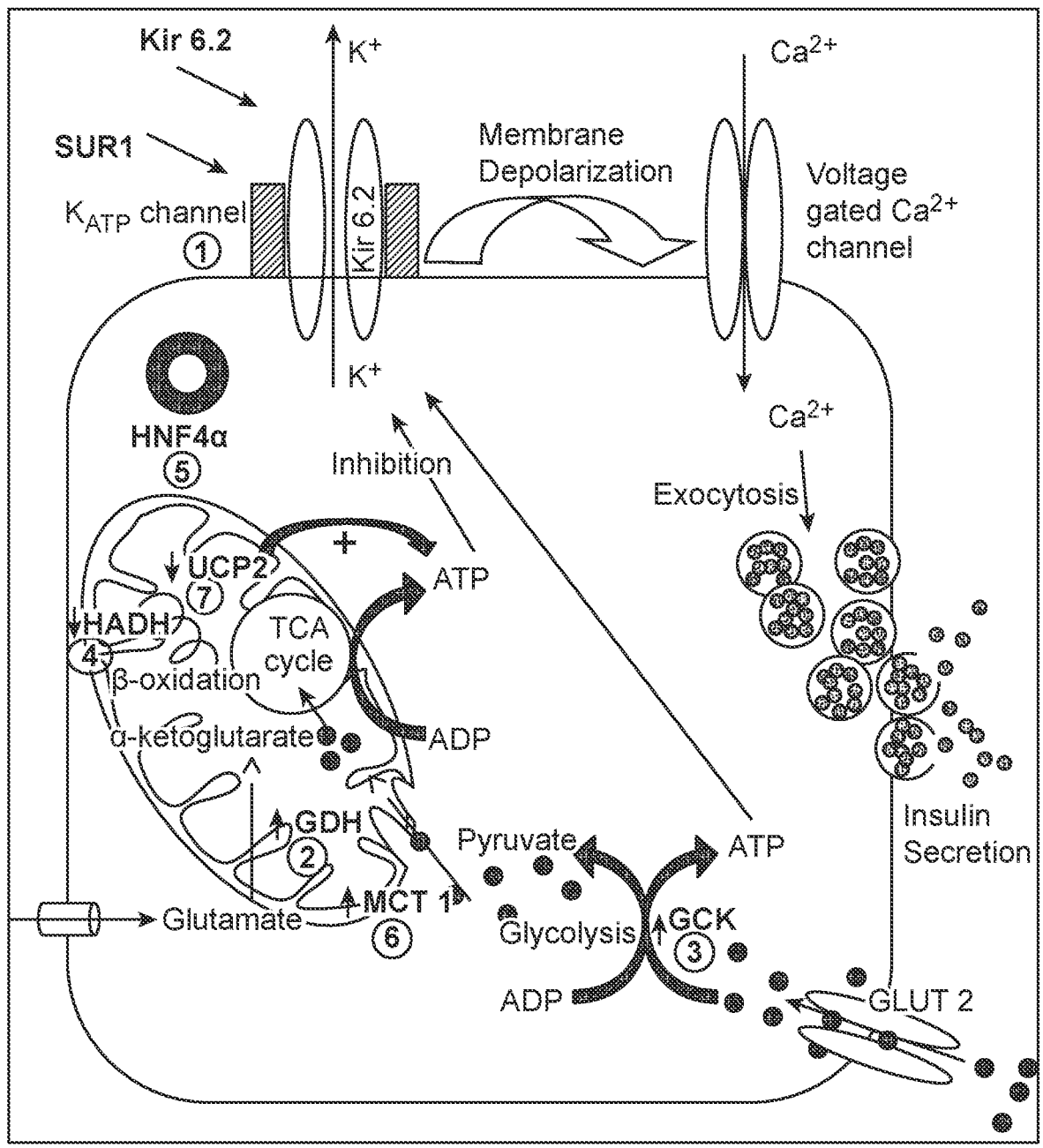
FIG. 1 shows the at least 7 genetic mutations in proteins (Kir6.2, SUR1, HNF4a, UCP2, HADH, GDH, MCT 1, and GCK) that ultimately lead to upregulation of insulin secretions. Standard treatment with diazoxide to modulate the Kir6.2 channel may be not effective in patients that have Kir6.2 mutations, which instead can be treated with glucagon.

Disclosed herein are compositions of glucagon analogs and methods of use thereof. In various embodiments, a glucagon analog can be stable in solution at a physiological pH. In some embodiments, physiological pH is between about pH 6.8 and pH 8. In other embodiments, a glucagon analog can be stable in solution at a physiological pH of about pH 7.4. In various embodiments, a glucagon analog's stability in solution can be indicated by the glucagon analog resistance to fibrillation, resistance to chemical degradation, or a combination thereof. The glucagon analog can comprise at least one mutation in a region between residue 22 and residue 27. In various embodiments the glucagon analog can be at least 90%, 95%, or 99% pure. In various embodiments, the glucagon analog can have at least 10%, 20%, 30%, 40%, 50%, 60%, 70%, 80%, or 90% glucagon receptor agonist activity of native glucagon. In various embodiments, the glucagon analog can be in a pharmaceutical composition with a pharmaceutically acceptable diluent. The pharmaceutical composition can be formulated for intravenous injection.

Disclosed herein are methods for producing a fusion peptide that can be purified and cleaved into a glucagon analog, and the glucagon analog produced according to the methods. In various embodiments, the method includes induction, inclusion body isolation, affinity column purification, and chemical cleavage. In various embodiments, methods and compositions described herein utilize an expression vector to make the glucagon analog described herein. In some aspects, by combining molecular expression technologies that employ genetically-malleable microorganisms such as *E. coli* cells to synthesize a glucagon analog with post-expression isolation and modification, one can synthesize a glucagon analog rapidly and efficiently. In various embodiments, methods and compositions described herein can produce fusion peptides that can be purified using affinity separation and cleaved with a chemical reagent to release a target peptide, including a glucagon analog.

In various embodiments, methods and compositions described herein are directed to a vector that encodes an inclusion body targeting sequence, an affinity tag to facilitate purification, and a specific amino acid sequence that facilitates selective chemical cleavage. Variously, the inclusion body targeting amino acid sequence can comprise from about 1 to about 125 amino acids of a ketosteroid isomerase protein or residues of oleosin, preferably residues up to residues 1-52, with or without amino acid substitutions. Such amino acid substitutions can improve chromatographic purification. The affinity tag sequence can comprise a poly-histidine, a poly-lysine, poly-aspartic acid, or poly-glutamic acid. In one embodiment, the vector further comprises an expression promoter located on the 5' end of the affinity tag sequence. In one embodiment, methods and compositions described herein are directed to a vector that codes for a specific sequence that facilitates selective chemical cleavage to yield a peptide of interest following purification. Such chemically cleavable amino acid sequences include Trp, His-Met, or Pro-Met.

In various embodiments, processes according to methods and compositions described herein provide a high yield of glucagon analogs with high purity. These glucagon analogs can also be more stable in solution compared to native glucagon. In various embodiments, glucagon analogs produced according to methods and compositions described herein can be R&D grade or clinical grade.

Peptide and protein hormones can be involved in the endocrine system. Peptide hormones can interact with different cell types through cell surface and intracellular receptors to regulate various aspects physiology, including homeostasis (e.g., glucose homeostasis and calcium homeostasis) and immune system regulation. Natural peptide hormones can be produced in various organs and tissues, including the pituitary gland (e.g., prolactin, adrenocorticotropic hormone, and growth hormone); the heart (e.g., atrial-natriuretic peptide or atrial natriuretic factor); the pancreas (e.g., glucagon, insulin, and somatostatin); the gastrointestinal tract (e.g., cholecystokinin, gastrin, and glucagon-like peptide-1); the parathyroid (e.g., parathyroid hormone); and adipose tissue stores (e.g., leptin). Some peptide hormones function as neurotransmitters (e.g., neuropeptides). Binding of a peptide hormone to a receptor (e.g., a cell surface receptor or an intracellular receptor) can trigger signal transduction resulting in cellular responses.

Irregular release or misregulation of peptide hormones can result in disease conditions, including, but not limited to, diabetes mellitus, congenital hyperinsulinism (CH), thyroid disease and obesity. In some cases where there is an insufficient amount of peptide hormone produced and/or released, synthetically or recombinantly produced peptide hormones can be administered to alleviate symptoms associated with the insufficient amount of endogenous peptide hormone.

For example, blood glucose levels can be primarily regulated by the glucoregulatory hormones, such as insulin, glucagon, amylin, and incretins (e.g., glucagon-like peptide-1, GLP-1). Glucoregulatory hormones can function to maintain circulating glucose concentrations within a desired range. Low blood glucose levels can stimulate the release of glucagon by alpha cells of the pancreas. Liver cells, in response to glucagon, can convert glycogen into glucose in a process referred to as glycolysis. The glucose can be released into the bloodstream, thereby increasing blood glucose levels. However, when blood glucose levels rise, whether as a result of glycogen conversion or from digestion of food, insulin can be released from the pancreas. Insulin can stimulate liver cells to convert glucose into glycogen in a process referred to as glycogenesis, thereby decreasing blood glucose levels. Together, glucagon and insulin can function in a feedback system to maintain blood glucose levels at a stable level. Amylin, a peptide co-secreted with insulin from the pancreas, can play a role in blood glucose regulation by slowing gastric emptying and inhibiting digestive secretion. Incretins, which can include glucagon-like peptide-1 (GLP-1), are a group of metabolic hormones that can stimulate a decrease in blood glucose levels. Glucagon-like peptide-1 (GLP-1) can be secreted primarily from the intestinal L-cells in response to food and modulates nutrient homeostasis via actions exerted in multiple tissues and cell types.

Irregular release or misregulation of any of the above mentioned peptide hormones can result in various medical conditions, including hyperglycemia and hypoglycemia. Chronic irregularities in the levels of these hormones can result in conditions including diabetes mellitus type 1, also referred to as type 1 diabetes. In some cases, glucoregulatory peptides, such as those produced synthetically or recombinantly, may be administered to treat conditions associated with misregulation of glucoregulatory hormones. For example, insulin peptides, glucagon peptides, and/or glucagon-like peptide-1 (GLP-1) peptides, analogs or fragments thereof can be administered to treat conditions associated with the irregular release or misregulation of peptide hormones.

Peptide hormones including glucoregulatory hormones such as glucagon or analogs thereof can be produced using methods described herein and administered as a peptide therapy. Furthermore, the goal of developing an artificial pancreas can be greatly advanced with the advent of novel solution-stable glucagon.

Unless defined otherwise, all technical and scientific terms used herein have the same meaning as commonly understood by a person of ordinary skill in the art.

The term "analog," as used herein, can refer to a protein that may be structurally and/or functionally similar to a native protein, for example a protein such as native glucoregulatory peptide (e.g., glucagon). An analog can be structurally and/or functionally similar to a native protein, but is different in other various aspects, such as protein size (e.g., number of amino acids, molecular weight, diameter, etc.), amino acid sequence, amino acid composition, and tertiary structure.

As used herein, the term "peptide" can mean any polymer comprising amino acids linked by peptide bonds. The term "peptide" can include polymers that are assembled using a ribosome as well as polymers that are assembled by enzymes (i.e., non-ribosomal peptides) and polymers that are assembled synthetically. In various embodiments, the term "peptide" can be considered synonymous with "protein," or "polypeptide." In various embodiments, the term "peptide" can be limited to a polymer of greater than 50 amino acids, or alternatively, 50 fewer amino acids. In various embodiments, the term "peptide" can include only amino acids as monomeric units for the polymer, while in various embodiments, the term "peptide" can include additional components and/or modifications to the amino acid backbone. For example, in various embodiments, the term "peptide" can be applied to a core polymer of amino acids as well as derivatives of the core polymer, such as core polymers with pendant polyethylene glycol groups or core polymers with amide groups at the amino or carboxy terminus of the amino acid chain. The terms can apply to naturally occurring amino acid polymers as well as amino acid polymers comprising one or more modified amino acids. In some cases, the polymer can be interrupted by non-amino acids. The terms can include amino acid chains of any length, including full length proteins, and proteins with or without secondary and/or tertiary structure. The terms also can encompass an amino acid polymer that has been modified, for example, by disulfide bond formation, glycosylation, lipidation, acetylation, phosphorylation, oxidation, and any other manipulation such as conjugation with a labeling component.

As used herein, the terms "amino acid" and "amino acids," generally can refer to natural and non-natural amino acids, including, but not limited to, modified amino acids and amino acid analogs. Modified amino acids can include natural amino acids and non-natural amino acids, which have been chemically modified to include a group or a chemical moiety not naturally present on the amino acid. Amino acid analogs can refer to amino acid derivatives. The term "amino acid" can include both D-amino acids and L-amino acids. Peptides, including 1) synthetically and recombinantly produced peptides that can mimic the function and/or properties of naturally occurring peptides and 2) engineered peptides that can possess alternative biological properties compared to a naturally occurring peptide (e.g., antagonism or agonism of a cellular receptor), can be investigated as therapeutic molecules (e.g., peptide therapeutics). Peptide therapeutics can include synthetic peptide hormones administered, for example, to treat homeostatic imbalance, such as glucoregulatory hormones administered to treat blood-glucose homeostatic imbalance.

As used herein, "consisting essentially of" can exclude those features not listed herein that would otherwise alter the operation of methods and compositions described herein. However, the use of the phrase "consisting essentially of" may not exclude features that do not alter the operation of the required components.

As used herein, the term "patient" can include members of the animal kingdom including but not limited to human beings. As used herein, the term "mammalian host" can include members of the animal kingdom including but not limited to human beings. The term "mammal" is known in the art, and exemplary mammals can include human, primate, bovine, porcine, canine, feline, and rodent (e.g., mice and rats).

As used herein, the term "diabetes" can be a hormonal disorder, the term "Type I diabetes" can mean insulin-dependent diabetes mellitus (IDDM), and the term "Type II diabetes" can mean non insulin-dependent diabetes mellitus (NIDDM).

As used herein, a "promoter" can be any sequence of DNA that is active, and controls transcription in a eukaryotic cell. The promoter can be active in mammalian cells. The promoter can be constitutively expressed or inducible. The promoter can be inducible by an external stimulus. The promoter can be inducible by hormones or metabolites. The promoter be regulated by glucose. The promoter can be a pyruvate kinase gene promoter. For example, the promoter can be a hepatocyte-specific L-type pyruvate kinase gene promoter.

As used herein, the abbreviations for the natural L-enantiomeric amino acids are conventional and are as follows: alanine (A, Ala); arginine (R, Arg); asparagine (N, Asn); aspartic acid (D, Asp); cysteine (C, Cys); glutamic acid (E, Glu); glutamine (Q, Gln); glycine (G, Gly); histidine (H, His); isoleucine (I, Ile); leucine (L, Leu); lysine (K, Lys); methionine (M, Met); phenylalanine (F, Phe); proline (P, Pro); serine (S, Ser); threonine (T, Thr); tryptophan (W, Trp); tyrosine (Y, Tyr); valine (V, Val). These amino acids can also be referred to as naturally occurring amino acids.

Glucagon Analogs

Glucagon can be effective for the treatment of a condition involving hypoinsulinism or hypoglycemia. For example, glucagon can be effective for both short-term and long-term treatment of severe forms of CH. However, the instability of glucagon in solution can create storage problems, administration problems, and potential complications due to infusion tube blockage.

Glucagon can be unstable in solution at a physiological pH. The instability of glucagon in solution can be attributed to both thermodynamic properties and chemical properties; however one additional aspect of instability for glucagon can be the propensity for fibrillation which can significantly limit both storage and usage. Fibrillation can be a propensity to undergo an irreversible non-covalent polymerization process which can cause the glucagon molecules to aggregate and form insoluble linear fibrils. Regions in glucagon, which can be referred to amyloidgenic regions or aggregation prone regions, can be associated with fibrillation and aggregation of glucagon. Glucagon can form many different morphological types of fibrils which can be dependent on pH, temperature, concentration and ionic strength conditions.

The fibrillation process can be multistep and can comprise a number of intermediate oligomeric species that gradually converge from a native monomeric conformation to the beta sheet structure of fibrils similar to amyloid. In addition, a prefibrillar oligomeric species can rearrange into fibrils.

This fibrillation process may be one of the primary reasons that glucagon cannot be formulated in a stable solution for pharmaceutical applications, which may have limited the use of glucagon to treat a variety of conditions because fibrillation process can cause both a gradual attenuation of the pharmacological potency, leading to dosage issues, as well as administration problems due to infusion tube clogging.

Long term thermodynamic stability and chemical stability of glucagon can be affected by pH and temperature. In addition, there are a number of secondary factors which can influence long-term stability. These include the type of crystal structure, the presence of bacteriostatic agents (phenol, m-cresol), buffering reagents (phosphate, TRIS), isotonicity additives (glucose, glycerol, NaCl), and substances added to protract glucagon's time of action profile (protamine sulfate and $Zn^{++}$). One aspect of glucagon stability can be the tendency of glucagon to fibrillate. The fibrillation of glucagon can be ascribed to hydrophobic regions at both the N- and C-terminus. These hydrophobic regions can also be referred to as aggregation prone regions of native glucagon. For example, a "hydrophobic patch" can comprise residues Phe6, Tyr10, Tyr13, or a combination thereof. (Unson, C. G., $Biopolymers$, 66(4): 218-35 (2002); Sondergaard Pedersen, J. et al., $Biochemistry$ 45(48): 14503-12 (2006)). A hydrophobic patch can refer to a cluster of neighboring apolar atoms or amino acid residues that can be on a given peptide surface and solvent accessible. Mutations in the hydrophobic patch can confer resistance to fibrillation as compared to fibrillation of native glucagon. Mutations in an aggregation prone region can confer resistance to fibrillation as compared to fibrillation of native glucagon. In some aspects, a mutation in Phe6, Tyr10, Tyr13, or a combination thereof can confer resistance to glucagon analog fibrillation compared to native glucagon fibrillation. Chemical stability of glucagon can depend, at least in part, on the chemical degradation of glucagon which is related to the deamidation of Asn and Gln side chains in glucagon. Deamidation can indicate chemical instability.

In contrast, a glucagon analog as described herein can be stable in solution at physiological pH. A glucagon analog can be stable in solution at a physiological pH between about pH 6 and pH 8. A glucagon analog can be stable in solution at a physiological pH of about 7.4. Glucagon analogs can encompass a group of structurally-related proteins with mutations relative to native glucagon. These mutations can be substitutions, insertions, deletions, or a combinations thereof. Substitutions or insertions can be made with naturally occurring amino acids or non-naturally occurring amino acids. For example, a residue in native glucagon can be mutated to Ala in a glucagon analog. Native glucagon can have the sequence SEQ ID NO: 20 (HSQGTFTSDYSKY-LDSRRAQDFVQWLMNT).

Determination of a more stable glucagon analog can be based upon a sparse matrix that encompasses two types of amino acid substitutions in native glucagon. The first type of substitution can minimize the primary mode of fibrillation and the second type of substitution can reduce the primary mode of chemical degradation, which can be the deamidation of Asn and Gln side chains. Any amino acid residue except Cys and Asn can be used to make the substitutions, and can be substituted in a random order at 6 (r) positions from residues 22 to 27 of native glucagon. The initial matrix can be determined using the following two initial rules: eliminate sequences containing Asn, Gln, Cys or Met; and eliminate sequences with a calculated aggregation propensity greater than 1.0, see FIG. 2B. Aggregation propensity can be calculated using AGGRESCAN, which is based on natural amino acids aggregation-propensity derived from in vivo experiments and on the assumption that short and specific sequence stretches modulate protein aggregation. (See Conchillo-Sole, O. et al., $BMC\ Bioinformatics$, 8:65 (2007)). A glucagon analog can be determined to have a greater resistance to fibrillation if it has a decreased computed aggregation score compared to native glucagon and decreased experimental aggregation after a time period in solution. For example, a timer period can be at least 7 days. Aggregation propensity can also be decreased by a mutation in the glucagon analog in a region corresponding to an aggregation prone region of native glucagon. The subsequent set of sequences can then be arranged in a matrix from low to high isoelectric point on the first axis and aggregation propensity on the other axis. These glucagon analogs with improved resistance to fibrillation can be further optimized by comparing substitutions made to improve resistance to fibrillation with substitutions made to improve resistance to chemical degradation in parallel using an agitation Thioflavin-T (Th-T) fluorescence assay (to test for resistance to fibrillation/aggregation) combined with quantitative HPLC analysis (to test for thermodynamic stability). Thermodynamic stability can be indicated by recovery of at least 80% of a glucagon analog after a time period of at least 7 to 180 days. For example, a glucagon analog can be thermodynamically stable if at least 80% or the glucagon analog is undegraded or unaggregated after a time period in solution, such as a time period of at least 7 days. Glucagon analogs with thermodynamic stability can then be tested for chemical stability using LC-MS/MS, which can measure the deamidation of the glucagon analog. This can be measured after a time period of at least 7 to 180 days. Low deamidation can indicate resistance to chemical degradation. Low deamidation can be compared to native glucagon over the same time period. For example, a glucagon analog can be chemically stable if deamidation of the glucagon analog is reduced relative to native glucagon after a time period in solution, such as a time period of at least 7 days. Finally, analogs showing both thermodynamic stability and chemical stability can be screened for glucagon receptor agonist activity using a FLIPR assay. In one embodiment, a glucagon analog can have at least 10%, 20%, 30%, 40%, 50%, 60%, 70%, 80%, or 90% glucagon receptor agonist activity of native glucagon. The α-helical structure of the C-terminal of glucagon can be involved in the ability of glucagon to bind to the glucagon receptor. The important residues for maintaining the α-helical structure, and therefore also the binding affinity of a glucagon analog to the glucagon receptor, can be Phe22, Val23, Trp25, Leu26, Met27, Asp15, or a combination thereof. In some embodiments, the C-terminal of the glucagon analog maintains a stabilized α-helical structure of a C-terminal of native glucagon. α-helices can be stabilized by substituting certain amino acids with poor propensities for forming an α-helix with other amino acids with high propensities for forming an α-helix. For example, substituting a proline amino acid with an alanine amino acid. Other non-limiting examples of amino acids with a poor propensity for forming an α-helix can be glycine. In contrast, other non-limiting examples of amino acids with a high propensity for forming an α-helix can be methionine, leucine, glutamate, and lysine. In some embodiments, a glucagon analog comprising at least one mutation in a region between amino acid residue 22 and amino acid residue 27 creates an α-helix stabilization.

TABLE 1

Exemplary Glucagon Analog Sequences.

| SEQ ID NO: | SEQUENCE |
|---|---|
| 1 | HSQGTFTSDYSKYLDSRRAQDFVQELANT |
| 2 | HSQGTFTSDYSKYLDSRRAQDFVQKLANT |
| 3 | HSQGTFTSDYSKYLDSRRAQDFAQELANT |
| 4 | HSQGTFTSDYSKYLDSRRAQDFAQKLANT |
| 5 | HSQGTFTSDYSKYLDSRRAQDFVQDLANT |
| 6 | HSQGTFTSDYSKYLDSRRAQDFVQHLANT |
| 7 | HSQGTFTSDYSKYLDSRRAQDFVQDLADT |
| 8 | HSQGTFTSDYSKYLDSRRAQDFVQDLAET |
| 9 | HSQGTFTSDYSKYLDSRRAQDFVQKLENT |
| 10 | HSQGTFTSDYSKYLDSRRAQDFVEKLENT |
| 11 | HSQGTFTSDYSKYLDSRRAQDFVEKLEST |
| 12 | HSQGTFTSDYSKYLDSRRAQDFVQKLLNT |
| 13 | HSQGTFTSDYSKYLDSRRAQDFVQKLLST |
| 14 | HSQGTFTSDYSKYLDSRRAQDFVEKLLST |
| 15 | HSQGTFTSDYSKYLDSRRAQDFVEKLEKT |
| 16 | HSQGTFTSDYSKYLDSRRAQDFVEKLANT |
| 17 | HSQGTFTSDYSKYLDSRRAQDFVEKLAST |
| 18 | HSQGTFTSDYSKYLDSRRAQDFVAKLANT |
| 19 | HSQGTFTSDYSKYLDSRRAQDFVAKLAKT |

In one embodiment, a glucagon analog variant can be any one of SEQ ID NO: 1-SEQ ID NO: 19. In some embodiments, a glucagon analog variant can have at least 80%, 85%, 90%, 95%, 98%, or 99% sequence identity with any one of SEQ ID NO: 1-SEQ ID NO: 19, or a fragment thereof.

In one embodiment, glucagon analogs with exemplary stability properties can include those glucagon analogs identified computationally as having a calculated aggregation propensity of less than one. In other embodiments, resistance to fibrillation can comprise having a decreased computed aggregation score compared to native glucagon and decreased experimental aggregation after a time period of at least 7 days in solution. In another embodiment, glucagon analogs with decreased fibrillation can have decreased aggregation as compared to native glucagon aggregation after a time period of at least 7, at least 14, at least, at least 21, at least 42, at least 63, at least 91 or at least 180 days. In some embodiments, a glucagon analog maintains at least 95% potency for at least 2 years when stored at 4° C. In other embodiments, a glucagon analog maintains at least 95% potency for at least 3 months when at 40° C.

A glucagon analog produced according to methods and compositions described herein can have differing levels of residual components from known peptide processes of production. For example, in comparison with a glucagon analog of the same sequence produced according to conventional recombinant processes, a glucagon analog produced according to methods and compositions described herein can be expected to have fewer residual cellular contaminants upon initial purification. Alternatively, in comparison with a glucagon analog of the same sequence produced by conventional synthetic processes, a glucagon analog produced according to methods and compositions described herein can be expected to have fewer residual chemical contaminants upon initial purification. A glucagon analog purified as described herein can be at least 90%, 95%, or 99% pure.

Vectors

Also provided herein are vectors that can produce glucagon analogs. A vector can encode an expression tag, a cleavage tag, and/or a glucagon analog sequence. The expression tag can comprise an amino acid sequence having at least 80% sequence identity to SEQ ID NO: 21 (MKAIFVLKGSLDRDPE-FPSDKPHHKKHHKKHHSSGSLE). The expression tag may comprise an amino acid sequence having at least 85%, 90%, 95%, 99% or 100% sequence identity to SEQ ID NO: 21 (MKAIFVLKGSLDRDPE-FPSDKPHHKKHHKKHHSSGSLE). The expression tag can further comprise an affinity tag, such as charged tag for ion exchange affinity chromatography or capture. The affinity tag sequence can comprise a poly-histidine, a poly-lysine, poly-aspartic acid, poly-glutamic acid, or combinations thereof. A cleavage tag can facilitate selective chemical cleavage to yield a peptide of interest following purification. Such chemically cleavable amino acid sequences can include Trp, His-Met, and Pro-Met. The vector can further comprise a nucleotide sequence that can encode an inclusion-directing peptide. Variously, the inclusion body targeting amino acid sequence can comprise a peptide sequence derived from a ketosteroid isomerase, an inclusion-body directing functional fragment of a ketosteroid isomerase, an inclusion-body directing functional homolog of a ketosteroid isomerase, a BRCA2 peptide, an inclusion-body directing functional fragment of BRCA2, and an inclusion-body directing functional homolog of BRCA2. In some embodiments, the vector further comprises an expression promoter located on the 5' end of the affinity tag sequence.

A method for producing a peptide using a vector can comprise the steps of: a) cleaving a vector with a restriction endonuclease to produce a cleaved vector; b) ligating the cleavage site to one or more nucleic acids, wherein the nucleic acids can encode a glucagon analog having at least a base overhang at each end configured and arranged for ligation with the cleaved vector to produce a second vector suitable for expression of a fusion peptide; c) transforming the second vector into suitable host cell; d) incubating the host cell under conditions suitable for expression of the fusion peptide; e) isolation of inclusion bodies from the host cell; f) solubilization and extraction of the fusion peptide from the inclusion bodies; g) binding of the fusion peptide to a suitable affinity material; h) optionally, washing of bound fusion peptide to remove impurities; and i) cleaving the fusion peptide to release the glucagon analog. A vector can include enhancer elements. Enhancer elements, which can control transcription, can be inserted into the vector construct for the production of glucagon analogs, and can be used to enhance the expression of the glucagon analog encoded in the vector.

Methods of producing glucagon analogs described herein can provide a high yield of glucagon analog with high purity, such as a purity of at least 95%, 96%, 97%, 98%, 99% purity or greater. Glucagon analogs produced may be R&D grade peptides or clinical grade therapeutics. Native glucagon can also be produced using the methods described herein.

The glucagon encoded in the vector can be native glucagon, naturally occurring glucagon analogs, non-naturally-occurring glucagon analogs, or naturally-occurring glucagon analogs with non-natural substitutions, deletions, or additions. The native glucagon or glucagon analog can be modified chemically or biologically following isolation to yield a derivative of the native glucagon or glucagon analog.

Inclusion-Body Directing Peptides

Inclusion bodies can be composed of insoluble and denatured forms of a peptide and can be about 0.5-1.3 µm in diameter. These dense and porous aggregates can help to simplify recombinant protein production since they can have a high homogeneity of the expressed protein or peptide, can result in lower degradation of the expressed protein or peptide because of a higher resistance to proteolytic attack by cellular proteases, and can be easy to isolate from the rest of the cell due to differences in their density and size relative to the other cellular components. Once isolated, the inclusion bodies can be solubilized to allow for further manipulation and/or purification.

An inclusion-body directing peptide can be an amino acid sequence that can help to direct a newly translated protein or peptide into insoluble aggregates within the host cell. Prior to final isolation, in various embodiments, a glucagon or glucagon analog can be produced as a fusion peptide where the fusion peptide can include, as part of its sequence of amino acids, an inclusion-body directing peptide. Methods and compositions described herein are applicable to a wide range of inclusion-body directing peptides as components of the expressed fusion glucagon or glucagon analog.

In various embodiments, the inclusion-body directing peptide can be a ketosteroid isomerase (KSI) sequence, a functional fragment thereof, or a functional homolog thereof. In various embodiments, the inclusion-body directing peptide can be a BRCA-2 sequence, a functional fragment thereof, or a functional homolog thereof.

Affinity Tag Peptides

According to methods and compositions described herein, a wide variety of affinity tags can be used. Affinity tags can be specific for cations, anions, metals, or any other material suitable for an affinity column. In one embodiment, any peptide not possessing an affinity tag can elute through the affinity column leaving the desired fusion peptide bound to the affinity column via the affinity tag.

Specific affinity tags can include poly-lysine, poly-histidine, poly-glutamic acid, or poly-arginine peptides. For example, the affinity tags can be 5-10 lysines (SEQ ID NO: 22), 5-10 histidines (SEQ ID NO: 23), 5-10 glutamic acids (SEQ ID NO: 24), or 5-10 arginines (SEQ ID NO: 25). In various embodiments, the affinity tag is a hexa-histidine sequence (SEQ ID NO: 26), hexa-lysine sequence (SEQ ID NO: 27), hexa-glutamic acid sequence (SEQ ID NO: 28), or hexa-arginine sequence (SEQ ID NO: 29). Alternatively, the HAT-tag (Clontech) may be used. In various embodiments, the affinity tag is a His-Trp Ni-affinity tag. Other tags known in the art can also be used. Examples of tags can include, but are not limited to, Isopeptag, BCCP-tag, Myc-tag, Calmodulin-tag, FLAG-tag, HA-tag, MBP-tag, Nus-tag, GST-tag, GFP-tag, Thioredoxin-tag, S-tag, Softag, Streptavidin-tag, V5-tag, CBP-tag, and SBP-tag.

The histidine residues of a poly-histidine tag can bind with high affinity to Ni-NTA or TALON resins. Both of these resins can contain a divalent cation (Ni-NTA resins contain $Mg^{2+}$; TALON resins contain $Co^{2+}$) that can form a high affinity coordination with the His tag.

In various embodiments, the affinity tag has a pI (isoelectric point) that is at least one pH unit separate from the pI of a glucagon or glucagon analog. Such difference can be either above or below the pI of the glucagon or glucagon analog. For example, in various embodiments, the affinity tag has a pI that is at least one pH unit lower, at least two pH units lower, at least three pH units lower, at least four pH units lower, at least five pH units lower, at least six pH units lower, or at least seven pH units lower. Alternatively, the affinity tag can have a pI that is at least one pH unit higher, at least two pH units higher, at least three pH units higher, at least four pH units higher, at least five pH units higher, at least six pH units higher, or at least seven pH units higher.

In various embodiments, the affinity tag is contained within the native sequence of the inclusion body directing peptide. Alternatively, the inclusion body directing peptide can be modified to include an affinity tag. For example, in one embodiment, the affinity tag is a KSI, oleosin N-terminus, or BRCA2 sequence modified to include extra histidines, extra lysines, extra arginines, or extra glutamic acids.

In various embodiments, epitopes can be used such as FLAG (Eastman Kodak) or myc (Invitrogen) in conjunction with their antibody pairs.

Cleavage of a Glucagon Analog from a Fusion Peptide on an Affinity Column

Described herein are numerous methods that can be used for cleavage of the fusion peptides containing a glucagon analog on the affinity column. In general, the cleavage step can occur by introduction of a cleavage agent which can interact with the cleavage tag of the fusion peptide and can result in the cleavage of the fusion peptide and the release of the glucagon analog. Following cleavage, the affinity column can be flushed to elute the glucagon analog while the portion of the fusion peptide containing the affinity tag remains bound to the affinity column. Following elution of the glucagon analog, the eluting solution can be condensed to a desired concentration. The glucagon analog can be further processed and/or packaged for distribution or sale.

Control of the cleavage reaction can occur through chemical selectivity. For example, the cleavage tag can include a unique chemical moiety which can be absent from the remainder of the fusion peptide such that the cleavage agent selectively interacts with the unique chemical moiety of the cleavage tag.

In various embodiments, control of the cleavage reaction can occur through a unique local environment. A wide range of cleavage tags can be used. In some cases, the cleavage tag is a tryptophan at the amino terminus of the glucagon or glucagon analog. For example, the cleavage tag can include a chemical moiety that is present elsewhere in the fusion peptide, but the local environment differs resulting in a selective cleavage reaction at the cleavage tag. For example, in various embodiments, the cleavage tag includes a tryptophan and a charged amino acid side chain within five amino acids of the tryptophan. In various embodiments, the charged amino acid is on the amino terminus of the tryptophan amino acid. Upon cleavage with a cleaving agent, the amide bond connecting the tryptophan to the glucagon or glucagon analog can be cleaved, and the glucagon or glucagon analog can be released from the affinity column.

Alternatively, the cleavage tag can be a tryptophan at the amino terminus of the glucagon or glucagon analog, where the cleavage tag also can include an amino acid with a charged side-chain in the local environment of the tryptophan, such as within five amino acids on the upstream (i.e., amino) or downstream (i.e., carboxy) side of the tryptophan. The presence of an amino acid side-chain within five amino acids on the amino terminus of the tryptophan amino acid can allow for selectivity of cleavage of the tryptophan of the cleavable tag over any other tryptophans that can be present in the heterologous fusion peptide, for example, tryptophans as part of the inclusion body directing peptide or as part of the glucagon or glucagon analog. In some cases, an amino acid with a positively charged side chain such as lysine, ornithine, or arginine is within five, four, three, or two amino acid units, or is adjacent on the amino terminus to the tryptophan of the cleavable tag. In some cases, a glutamic acid amino acid is within five, four, three, or two amino acid units, or is adjacent on the amino terminus to the tryptophan of the cleavable tag.

The cleavage tag can be His-Met or Pro-Met. In some cases, the cleavage tag is an unnatural amino acid. Cells can be modified to enable the cells to produce peptides which can contain unnatural amino acids. For instance, modifications can be made to the protein biosynthetic machinery of E. coli which can allow the site-specific incorporation of an unnatural amino acid, O-methyl-L-tyrosine, in response to an amber stop codon (TAG) (Wang, et al., (2001) Science 292:498-500). Alternatively, numerous unnatural amino acids can be site-specifically incorporated into proteins in E. coli, yeast, or mammalian cells (Wang, et al., (2009) Chem Biol. 16(3):323-36). Incorporation of one or more unnatural amino acids can provide additional selectivity for cleavage at the unnatural amino acid over non-specific cleavage at other sites on the fusion peptide.

Heterologous fusion peptides produced by methods described herein can comprise unnatural amino acids. In some aspects, prokaryotic cells with modifications to the protein biosynthetic machinery produce such fusion peptides. Examples of such prokaryotic cells include E. coli. In some aspects the modifications comprise adding orthogonal tRNA/synthetase pairs. In some aspects four base codons encode novel amino acids. In some aspects, E. coli allow the site-specific incorporation of the unnatural amino acid O-methyl-L-tyrosine into a peptide in response to an amber stop codon (TAG) being included in an expression vector.

In various embodiments, control of the cleavage reaction can occur through secondary or tertiary structure of the fusion peptide containing a glucagon analog. For example, in various embodiments, where identical moieties are present in the cleavage tag and elsewhere in the fusion peptide, the other portions of the fusion peptide can fold in secondary or tertiary structure such as alpha-helices, beta-sheets, and the like, or through disulfide linkages to physically protect the susceptible moiety, resulting in selective cleavage at the cleavage tag.

In various embodiments, minor or even major differences in selectivity of the cleavage reaction for the cleavage tag over other locations in the fusion peptide can be amplified by controlling the kinetics of the cleavage reaction. For example, in various embodiments, the concentration of cleavage agent is controlled by adjusting the flow rate of eluting solvent containing cleavage agent. In various embodiments, the concentration of cleavage agent is maintained at a low level to amplify differences in selectivity. In various embodiments, the reservoir for receiving the eluting solvent contains a quenching agent to stop further cleavage of glucagon or glucagon analog that has been released from the column.

Moreover, various methods for removal of peptides from affinity columns can be excluded. For example, in some embodiments, the steps of removal can specifically exclude the step of washing an affinity column with a solution of a compound with competing affinity in the absence of a cleavage reaction. In one embodiment, the step of washing an affinity column with a solution of imidazole as a displacing agent to assist in removing a fusion peptide from an affinity column is specifically excluded. The concentration of imidazole can vary. For example, the concentration of imidazole to wash the column can include about 1-10 mM, 5-20 mM, 10-50 mM, 30-70 mM, 50-100 mM, 80-200 mM, 100-300 mM, 150-500 mM. Imidazole can be applied as a fixed concentration or as a gradient between two fixed concentration representing the lower and the upper limits. For example, a gradient of imidazole can be used to wash the column, starting from 1 mM and ending with 500 mM over a period of time.

In some cases, multiple cleavages can occur. For example, insulin is naturally produced from a proinsulin precursor requiring two cleavage events. Both cleavage events can be required in order for the mature insulin to be properly folded. Therefore, a vector designed for insulin production can comprise two cleavage tags. Preferably, when more than one cleavage tag is present, the distinct cleavage tags are orthogonal, or able to be cleaved with specificity by different cleavage agents. For example, one cleavage tag can be a methionine amino acid while the other cleavage tag may be a tryptophan amino acid.

Non-limiting examples of cleavage agents can include NBS, NCS, cyanogen bromide, $Pd(H_2O)_4$, 2-ortho iodobenzoic acid, DMSO/sulfuric acid, or a proteolytic enzyme.

In various embodiments, the cleavage agent can be selected from the group consisting of NBS, NCS, cyanogen bromide, $Pd(H_2O)_4$, 2-ortho iodobenzoic acid, DMSO/sulfuric acid, or a proteolytic enzyme.

In one embodiment, the cleavage reaction can involve the use of a mild brominating agent N-ibromosuccinimde (NBS) that can selectively cleave a tryptophanyl peptide bond at the amino terminus of the glucagon analog peptide. For example, in aqueous and acidic conditions, NBS can oxidize the exposed indole ring of the tryptophan side chain, thus initiating a chemical transformation that can result in cleavage of the peptide bond at this site. Accordingly, the active bromide ion can halogenate the indole ring of the tryptophan residue followed by a spontaneous dehalogenation through a series of hydrolysis reactions. These reactions can lead to the formation of an oxindole derivative which can promote the cleavage reaction.

In one embodiment, the cleavage reaction can involve the use of a mild oxidizing agent N¬chlorosuccinimide (NCS) that can selectively cleave a tryptophanyl peptide bond at the amino terminus of the glucagon or glucagon analog. For example, in aqueous and acidic conditions, NCS can oxidize the exposed indole ring of the tryptophan side chain, thus initiating a chemical transformation that can result in cleavage of the peptide bond at this site.

In some cases, enzymes can be employed to cleave the fusion protein. For example, serine or threonine proteases that can bind to either serine or threonine, respectively, can initiate catalytic mechanisms that can result in proteolysis can be used. Additional enzymes can include collagenase, enterokinase factor $X_A$, thrombin, trypsin, clostripain and alasubtilisin.

In some cases, the cleavage agent can be a chemical agent such as cyanogen bromide, palladium (II) aqua complex (such as $Pd(H_2O)_4$), formic acid, or hydroxylamine. For example, cyanogen bromide can be used to selectively cleave a fusion peptide at a methionine amino acid at the amino terminus of the glucagon or glucagon analog.

Downstream Processing

Glucagon or glucagon analog produced according to methods described herein can be further modified. For example, the C-terminus of the glucagon or glucagon analog can be connected to alpha-hydroxyglycine. At the desired time, the glucagon or glucagon analog, either as the isolated glucagon or glucagon analog, or as part of the fusion peptide, can be exposed to acid catalysis to yield glycolic acid and a carboxamide group at the carboxy terminus of the glucagon or glucagon analog. A carboxamide group at the carboxy terminus may be present in a variety of neuropeptides, and is thought to increase the half-life of various peptides in vivo.

Glucagon or glucagon analog produced according to methods described herein can be further modified to alter in vivo activity. For example, a polyethylene glycol (PEG) group can be added to a glucagon or glucagon analog.

Ribosomal Synthesis of a Fusion Peptide

Peptides can be produced by ribosomal synthesis, which can utilize transcription and translation to express peptides. Some peptides can be expressed in their native form in eukaryotic hosts, such as mammalian cell systems (e.g., Chinese hamster ovary (CHO) cells, human embryonic kidney (HEK) cells including HEK 293 and HEK 293F cells, HeLa cells, PC3 cells, Vero cells, and MC3T3 cells); yeast cell systems (e.g., *Saccharomyces cerevisiae*, *Bacillus subtillis*, and *Pichia pastoris*); and insect cell systems (e.g., Sf9, Sf21, and High Five strains). As an alternative, bacterial host expression systems, such as systems using *Escherichia coli* (*E. coli*), *Corynebacterium*, and *Pseudomonas fluorescens*, can be used.

A nucleic acid sequence, such as a DNA sequence, which can serve as a template for transcription in ribosomal synthesis may be provided in a vector. A vector can provide additional nucleotide sequences useful for protein expression via ribosomal synthesis. A vector can generally refer to one or more nucleotide sequences that are operably linked. The term "operably linked," as used herein, can refer to nucleotide sequences placed in a functional relationship with another nucleotide sequence. Nucleotide sequences of a vector can encode for a protein (e.g., protein coding sequence) such as a target peptide or can comprise vector elements such as control or regulatory sequences, selectable markers, promoters (e.g., inducible and constitutive), ribosomal binding sites, termination sequences, etc. Selectable markers, such as antibiotic resistance, can enable selective screening against the cells that do not contain the constructed vector with the gene of interest. Vectors can include hybrid promoters and multiple cloning sites for the incorporation of different genes. A vector can also include a nucleotide sequence encoding an expression tag and/or a cleavage tag. Non-limiting examples of expression vectors can include the pET system and the pBAD system (e.g., for bacterial expression systems); the pPIC system and the pYES system (e.g., for yeast expression systems); and the pcDNA system (e.g., for mammalian expression systems). The choice of nucleic acid vector and vector elements can be chosen for compatibility with the host expression system.

For example, the pET system can encompass more than 40 different variations on the standard pET vector. In some cases, the pET system can utilize a T7 promoter that is recognized specifically by T7 RNA polymerase. This polymerase can transcribe DNA five times faster than *E. coli* RNA polymerase, allowing for increased levels of transcription.

A vector can be designed to include sequences encoding for a heterologous fusion peptide comprising an expression tag such as SEQ ID NO: 21 (MKAIFVLKGSLDRDPE-FPSDKPHHKKHHKKHHSSGSLE), a cleavage tag, and a target peptide. In some cases, the vector further comprises nucleotide sequences encoding for an inclusion body directing peptide and/or an affinity tag. An affinity tag, such as, but not limited to, a sequence of charged amino acids (e.g., polyhistidine and/or polylysine), an AviTag, a FLAG-tag, an HA-tag, a Myc-tag, an SBP-tag, or combinations thereof, can also be included in the expression tag and can be used for purification processes. For example, a pET-19b vector to be used with bacterial expression systems can comprise nucleotide sequences encoding for an expression tag such as SEQ ID NO: 21 (MKAIFVLKGSLDRDPE-FPSDKPHHKKHHKKHHSSGSLE) or a fragment thereof, a cleavage tag, a target peptide such as a glucagon or glucagon analog, and optionally an inclusion body directing peptide and/or an affinity tag. Similarly, a pPIC vector to be used with yeast expression systems or a pcDNA vector to be used with mammalian expression systems can comprise nucleotide sequences encoding for an expression tag such as SEQ ID NO: 21 (MKAIFVLKGSLDRDPE-FPSDKPHHKKHHKKHHSSGSLE) or a fragment thereof, a cleavage, a target peptide such as a glucagon analog, and optionally a inclusion body directing peptide and/or an affinity tag.

The vector can be introduced into a host cell, such as a bacterial cell (e.g., *E. coli, Corynebacterium*, and *Pseudomonas fluorescens*) or a yeast cell (e.g., *Saccharomyces cerevisiae, Bacillus subtillis*, and *Pichia pastoris*), using any suitable method, including transformation, transfection, electroporation, and microinjection. For example, transformed *E. coli* cells can be plated onto agar containing an antibacterial agent to prevent the growth of any cells that do not contain a resistance gene, thereby selecting for cells that have been transformed. Colonies from the plating process can be grown in starter culture or broth according to standard cell culture techniques. For example, one colony from an agar plate is grown in a starter culture of broth, which may optionally contain an antibacterial agent. Typically, cells can be grown to a preselected optical density before being further processed to obtain fusion peptide. For example, cells can be grown to an optical density (OD) of about 0.1, about 0.2, about 0.3, about 0.4, about 0.5, about 0.6, about 0.7, about 0.8, or about 0.9. In some embodiments, the cells are grown to an optical density (OD) of about 0.5.

Once a vector is introduced into a host cell, the host cell can be used for heterologous peptide expression. With a vector comprising a constitutive promoter, expression of the heterologous fusion peptide can occur when the vector is introduced into the host cell. With a vector comprising an inducible promoter, expression of the desired heterologous fusion peptide can be induced or activated in a cell having a vector, for example using molecules that can activate an inducible promoter. For example, in *E. coli* cells, the lac operon can serve as an inducible promoter that can be activated under certain environmental conditions. *E. coli* can be capable of metabolizing the monosaccharide glucose. However, in order to metabolize the disaccharide lactose, the cells may need an enzyme known as α-galactosidase. Thus, low extracellular glucose concentrations and high lactose concentrations can induce the lac operon and the gene for α-galactosidase can be transcribed. In some cases, an inducible promoter such as the lac operon is situated upstream from the sequence coding for the fusion peptide. Upon induction of the lac operon, transcription of the sequence coding for the desired fusion peptide can occur.

The term "activation" can refer to the removal of repressor protein. A repressor protein can be generally allosteric meaning it can change shape when bound by an inducer molecule and dissociates from the promoter. This dissociation can allow for the transcription complex to assemble on DNA and initiate transcription of any genes downstream of the promoter. Therefore, by splicing genes produced in vitro into the bacterial genome, one can control the expression of novel genes. This trait can be used advantageously when dealing with inclusion bodies if the production and amassing of inclusion bodies becomes toxic enough to kill *E. coli*. For example, expression of the desired fusion peptide can be delayed until a sufficient population of cells has been cultured, and then the promoter can be induced to express a large amount of fusion peptide by removal of the repressor protein. Thus, the L-arabinose operon can be activated for increased protein expression at a desired time point. Specifically, the L-arabinose operon can be activated by both the addition of L-arabinose into the growth medium and the addition of IPTG, a molecule that can act as an activator to dissociate the repressor protein from the operator DNA. L-arabinose can bind to the AraC dimer causing the protein to release the $O_2$ site on the DNA and bind to the $I_2$ site. These steps can serve to release the DNA loop and can enable its transcription. Additionally, the cAMP activator protein (CAP) complex can stimulate AraC binding to $I_1$ and $I_2$— a process that can be initiated with IPTG.

In some cases, cells expressing only a fusion peptide with an expression tag, a cleavage tag, and the target peptide may not be able to produce large amounts of fusion peptide. The reasons for low production yields can vary. For example, the heterologous fusion peptide can be toxic to the host cell (e.g., the bacterial cell), thus causing the host cell to die upon production of certain levels of the fusion peptide. Alternatively, a glucagon or glucagon analog can be either poorly expressed or rapidly degraded in the bacterial system. In some cases, the glucagon or glucagon analog can be modified by the host cell, including modifications such as glycosylation. To remedy some or all of these problems, the desired fusion peptide can be directed to an inclusion body, thereby physically segregating the glucagon or glucagon analog from degradative factors in the cell's cytoplasm. Moreover, by physically aggregating the fusion peptide in an inclusion body, the subsequent separation of the fusion peptide from the constituents of the host cell and the media (i.e., cell culture or broth) can be performed more easily or efficiently. In some cases, the host cell can be modified for increased protein expression efficiency. For example, a bacterial cell, such as an *E. coli*, cell can be modified to be protease deficient.

Glucagon or glucagon analogs can be directed to inclusion bodies by an inclusion-body directing peptide as part of the heterologous fusion peptide. In some cases, an otherwise identical heterologous fusion peptide without an inclusion-body directing peptide has minimal or no tendency to be directed to inclusion bodies in an expression system. Alternatively, an otherwise identical heterologous fusion peptide without an inclusion-body directing peptide has some tendency to be directed to inclusion bodies in an expression system, but the number, volume, or weight of inclusion bodies can be increased by producing a fusion peptide with an inclusion-body directing peptide.

For example, methods have been described which allow α-human atrial natriuretic peptide (α-hANP) to be synthesized in stable form in *E. coli*. Eight copies of the synthetic α-hANP gene were linked in tandem, separated by codons specifying a four amino acid linker with lysine residues flanking the authentic N and C-termini of the 28 amino acid hormone. That sequence was then joined to the 3' end of the fragment containing the lac promoter and the leader sequence coding for the first seven N terminal amino acids of α-galactosidase. The expressed multidomain protein accumulated intracellularly into stable inclusion bodies and was purified by urea extraction of the insoluble cell fraction. The purified protein was cleaved into monomers by digestion with endoproteinase lys C and trimmed to expose the authentic C-terminus by digestion with carboxypeptidase B (Lennick et al., *Gene*, 61:103-112 (1987)).

Directing the glucagon or glucagon analog to an inclusion body by producing the glucagon or glucagon analog as part of a fusion peptide may lead to higher output of the fusion peptide. For example, the desired fusion peptide can be produced in concentrations greater than 100 mg/L. The desired fusion peptide can be produced in concentrations greater than about 200 mg/L, 250 mg/L, 300 mg/L, 350 mg/L, 400 mg/L, 450 mg/L, 500 mg/L, 550 mg/L, 600 mg/L, 650 mg/L, 700 mg/L, 750 mg/L, 800 mg/L, 850 mg/L, 900 mg/L, 950 mg/L, and 1 g/L, all amounts being prefaced by "greater than about." In some cases, the output of desired fusion peptide is greater than about 1.5 g/L, greater than about 2 g/L, or greater than about 2.5 g/L. The output of desired fusion peptide can be in the range of from about 500 mg/L to about 2 g/L, or from about 1 g/L to about 2.5 g/L. In some cases, the desired fusion peptide is produced in yields equal to or greater than 500 mg/L of media.

The inclusion-body directing peptide can be a ketosteroid isomerase (KSI) or inclusion-body directing functional fragment thereof. The inclusion-body directing functional fragment can have at least 25, at least 30, at least 35, at least 40, at least 45, at least 50, at least 55, at least 60, at least 65, at least 70, at least 75, at least 80, at least 85, at least 90, at least 95, or at least 100 amino acids. Ketosteroid isomerase can also include homologs of ketosteroid isomerase. Such homologs can have at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% sequence identity with the amino acid sequence of a ketosteroid isomerase. An expression system for a fusion peptide with a functional fragment or homolog of a ketosteroid isomerase can produce at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or greater than 100% of the amount of inclusion bodies produced by an otherwise identical expression system with a fusion peptide containing a complete ketosteroid isomerase peptide sequence.

Synthetic Fusion Peptide Synthesis

The heterologous fusion peptide can alternatively be made through solid phase peptide synthesis (SPPS) or liquid-phase peptide synthesis. SPPS can involve covalently linking amino acids in an ordered manner to form a synthetic peptide with a desired amino acid sequence. Solid supports, e.g., polystyrene resin, polyamide resin, polyethylene (PEG) hybrid polystyrene resin, or PEG-based resin, can be provided as a structural support for the elongation of the peptide, generally from the C-terminus to the N-terminus. Amino acids with "temporary" protecting groups, e.g., 9-fluorenylmethyloxycarbonyl group (Fmoc) or t-butyloxycarbonyl (Boc) protecting groups, can be added to the N-terminus of a growing peptide chain through iterations of various steps including deprotection, e.g., removal of protecting groups, and reaction steps, e.g., formation of peptide bonds.

Liquid-phase peptide synthesis similarly can add amino acids to a growing peptide chain in an ordered fashion, however, without the aid of a solid support. Liquid-phase peptide synthesis generally can require that the C-terminus of the first amino acid be protected and the growing peptide chain be isolated from the reaction reagents after each amino acid addition so that one amino acid is not unintentionally incorporated two or more times into the peptide chain.

In one embodiment, the solid phase peptide synthesis uses Fmoc protecting groups. The Fmoc protecting group can utilize a base labile alpha-amino protecting group. In an alternative embodiment, the solid phase peptide synthesis can use Boc protecting groups. The Boc protecting group can be an acid labile alpha-amino protecting group. Each method can involve distinct resin addition, amino acid side-chain protection, and consequent cleavage/deprotection steps. Generally, Fmoc chemistry can generate peptides of higher quality and in greater yield than Boc chemistry. Impurities in Boc-synthesized peptides can mostly be attributed to cleavage problems, dehydration and t-butylation. Once assembled on the solid support, the peptide can be cleaved from the resin using strongly acidic conditions, usually with the application of trifluoracetic acid (TFA). It can then be purified using reverse phase high pressure liquid chromatography (RP-HPLC), a process in which sample can be extruded through a densely packed column and the amount of time it takes for different samples to pass through the column (known as a retention time) can be recorded. As such, impurities can be separated out from the sample based on the principle that smaller peptides pass through the column with shorter retention times and vice versa. Thus, the protein being purified can elute with a characteristic retention time that can differ from the rest of the impurities in the sample, thus providing separation of the desired protein. Other examples of purification techniques can include size exclusion chromatography (SEC) and ion exchange chromatography (IEC).

Solid-phase peptide synthesis can generally provide high yields because excess reagents can be used to force reactions to completion. Separation of soluble byproducts can be simplified by the attachment of the peptide to the insoluble support throughout the synthesis. Because the synthesis can occur in the same vessel for the entire process, mechanical loss of material can be low.

In various embodiments, an inclusion body directing peptide can be excluded. Alternatively, an inclusion body directing peptide can be included to provide beneficial folding properties and/or solubility/aggregating properties.

Non-Ribosomal Fusion Peptide Synthesis

Fusion peptides can be produced by non-ribosomal synthesis. Such fusion peptides can include circular peptides and/or depsipeptides. Nonribosomal fusion peptides can be synthesized by one or more nonribosomal peptide synthetase (NRPS) enzymes. These enzymes can be independent of messenger RNA. Nonribosomal fusion peptides can have a cyclic and/or branched structure, can contain non-proteinogenic amino acids including D-amino acids, can have modifications like N-methyl and N-formyl groups, or can be glycosylated, acylated, halogenated, or hydroxylated. Cyclization of amino acids against the fusion peptide backbone can be performed, resulting in oxazolines and thiazolines; these can be further oxidized or reduced. On occasion, dehydration can be performed on serines, resulting in dehydroalanine.

The enzymes of an NRPS can be organized in modules that are responsible for the introduction of one additional amino acid. Each module can consist of several domains with defined functions, separated by short spacer regions of about 15 amino acids. A typical NRPS module can be organized as follows: initiation module, one or more elongation modules, and a termination module. The NRPS genes for a certain peptide can be organized in one operon in bacteria and in gene clusters in eukaryotes.

In some cases, an inclusion body directing peptide can be excluded. Alternatively, an inclusion body directing peptide can be included to provide beneficial folding properties and/or solubility/aggregating properties.

Separation of Fusion Peptide from Formation Media

Following production of the desired heterologous fusion peptides (e.g., in host cell expression systems), separation from the production media can be needed. Optionally, following separation, the desired fusion peptide and carrier can be concentrated to remove excess liquid. Numerous methods for separating fusion peptides from their formation media and subsequent handling can be adapted and used.

In some cases, fusion peptides can be directed to inclusion bodies. The cells used to produce the desired fusion peptides can be lysed to release the fusion peptides. For example, where the desired fusion peptide is aggregated in inclusion bodies, the cell can be lysed, followed by separation of the inclusion bodies from the production media and cellular detritus.

Any appropriate method of cell lysis can be used, including chemical lysis and mechanical lysis. For example, cells can be disrupted using high-power sonication in a lysis buffer. A lysis buffer containing Tris, sodium chloride, glycerol, and a protease inhibitor can be added before lysis. In some cases, a lysis buffer containing about 25 mM Tris pH 8.0, about 50 mM NaCl, about 10% glycerol, and the protease inhibitor 1000×PMSF can be added before lysis. Insoluble inclusion bodies can be collected using one or more washing steps and centrifugation steps. Wash buffers can include any reagents used for the stabilization and isolation of proteins. For example, wash buffers used can contain varying concentrations of Tris pH 8.0, NaCl, and Triton X100.

Targeting the desired fusion peptide to an inclusion body can result in higher initial purity upon lysis of the cell. For example, lysis of the cell and isolation of inclusion bodies through physical means such as centrifugation can result in an initial purity of greater than about 70%, great than about 75%, greater than about 80%, greater than about 85%, greater than about 90%, or greater than about 95% for the desired fusion peptide. In some cases, following cell lysis, inclusion bodies form a pellet and remain in the pellet rather than supernatant until a solubilization step. The pellet can be washed clean of the remaining cellular components, and insoluble inclusion bodies are solubilized in a buffer for further handling. Solubilization buffers can include urea or any other chaotropic agent necessary to solubilize the fusion peptide. The solubilization step can involve solubilizing the inclusion bodies in a chaotropic agent which can serve to disrupt the fusion peptides by interfering with any stabilizing intra-molecular interactions.

The solubilization buffer can include urea, guanidinium salts, or organic solvents. For example, a solubilization buffer can contain about 25 mM Tris pH 8.0, about 50 mM, NaCl, about 0.1 mM PMSF, and about 8M urea. In some cases, solubilization of inclusion bodies can occur with the addition of 8M urea as the sole chaotropic agent, and other chaotropic agents can be excluded. Alternatively, the solubilization buffer can exclude urea or guanidinium salts. For example, guanidinium salts can be excluded to avoid interference with further processing on an ion exchange column. As an additional example, high urea concentrations such as about 8M urea can be excluded to avoid denaturing proteases that can be included in the solubilization buffer.

In some cases, a minimal amount of solubilization buffer can be used. In the event that excess solubilization buffer is present, the solution can be processed to remove excess solvent prior to further purification In some cases, fusion peptides may not be directed to inclusion bodies. The fusion peptides can remain in the cytosol of the cell, or the fusion peptides can be secreted from the cell. Soluble fusion peptides can be isolated by any method, such as centrifugation, gel electrophoresis, pH or ion exchange chromatography, size exclusion chromatography, reversed-phase chromatography, dialysis, osmosis, filtration, or extraction.

Purification by Affinity Chromatography

Following cell lysis and initial isolation and solubilization of fusion peptides, the fusion peptides can be further purified by affinity chromatography, which is a highly selective process that relies on biologically-relevant interactions between an immobilized stationary phase and the fusion peptide to be purified. In some cases, the immobilized stationary phase can be a resin or matrix. Affinity chromatography can function by selective binding of the desired component from a mixture to the immobilized stationary phase, followed by washing of the stationary phase to remove any unbound material.

A wide variety of affinity chromatography systems can be used. For example, polyhistidine can bind with great affinity and specificity to nickel and thus an affinity column of nickel, such as QIAGEN nickel columns, can be used for purification. Alternatively, Ni-NTA affinity chromatography resin (available from Invitrogen) can be used. Metal affinity chromatography can be used as a basis for protein separations, wherein a specific metal chelating peptide on the N- or C-terminus of a protein can be used to purify that protein using immobilized metal ion affinity chromatography.

The affinity column can first be equilibrated with a buffer which can be the same as used for the solubilization of the fusion peptide. The column can then be charged with the solubilized fusion peptide, and the buffer can be collected as it flows through the column. In some cases, the column can be washed successively to remove urea and/or other impurities such as endotoxins, polysaccharides, and residual contaminants remaining from the cell expression system.

Glucagon Analog Administration

Glucagon analogs described herein can be administered as a single agent or as a combination to treat a subject in need thereof. A subject can be a human. A subject can be a mammal. A glucagon analog can be administered to treat a disease or disorder, for example diabetes including type I diabetes and type II diabetes, congenital hyperinsulinism, hypoglycemia, severe hypoglycemia, obesity, hyperglycemia, hyperinsulinemia, hypercholesterolemia, elevated blood levels of free fatty acids or glycerol, hyperlipidemia, hypertriglyceridemia, obesity, wound healing, tissue ischemia, atherosclerosis, hypertension, or AIDS. A glucagon analog can also be administered as part of a pharmaceutical composition. The pharmaceutical composition can comprise a glucagon analog and a pharmaceutically acceptable excipient or diluent. A pharmaceutically acceptable excipient or diluent can include buffers such as phosphate, citrate, and other organic acids; antioxidants including ascorbic acid and methionine; preservatives, polypeptides; proteins, such as serum albumin or gelatin; hydrophilic polymers; amino acids; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes; and/or non-ionic surfactants or polyethylene glycol.

Glucagon analogs can be administered to treat various diseases via various routes including, but not limited to, parenteral routes such as intravenous injection, intra-arterial injection, intraosseous infusion, intra-muscular injection, intracerebral injection, intrathecal injection, and subcutaneous injection; enteral routes such as oral administration and rectal administration topical administration; and topical routes such as epicutaneous administration and nasal administration. With intravenous administration, glucagon or glucagon analogs can be directly and fully available in the bloodstream and can be distributed via systemic circulation to the point where a pharmacological effect may occur place. A glucagon analog can be administered via a patch or a pump. A glucagon analog can be administered via a closed loop pump.

Various strategies can be employed to increase the bioavailability of administered drugs, such as chemical modification, formulation vehicles and use of enzyme inhibitors, absorption enhancers and mucoadhesive polymers. Enzyme inhibitors can be co-administered with peptide therapeutics to increase bioavailability by inhibiting the activity of proteases (e.g., trypsin, chymotrypsin, elastase, pepsin, and carboxypeptidases) which cleave amino acid side chains with varying specificity. Enzyme inhibitors can be more effective in the large intestine than the small intestine due to a larger quantity and variety of proteases within the small intestine. Examples of enzyme inhibitors include trypsin inhibitors, which are a type of serine protease inhibitor that reduces the biological activity of trypsin. Examples of trypsin inhibitors include soybean trypsin inhibitor, which is an inhibitor of chymotrypsin; Bowman-Birk inhibitor (BBI) proteins from legumes (e.g., soybean, pea, lentil, and chickpea); bovine pancreas trypsin inhibitor (BPTI); and ovomucin (trypsin inhibitor found in egg white, e.g., chicken egg white, duck egg white, and turkey egg white).

In some cases, a glucagon analog described herein can be administered in combination with native glucagon. In other cases, a glucagon analog can be administered in combination with another glucagon analog.

In some cases, peptide therapeutics may be administered in a pharmaceutical composition using an appropriate diluent.

The compositions and methods provided herein can be useful for the treatment of a plurality of diseases, conditions, preventing a disease or a condition in a subject or other therapeutic applications for subjects in need thereof.

In one embodiment, a dosage form comprising one or more glucagon analogs according to the invention may be used for clinical purpose. A clinical purpose includes, but is not limited to, diagnosis, prognosis, therapy, clinical trial, and clinical research. In one embodiment, glucagon analogs are used for studying pharmacokinetics/pharmacodynamics. In one embodiment, a dosage form may be formulated for a particular delivery route. A delivery route includes, but is not limited to, oral, nasal, rectal, intravascular, intraperitoneal, intramuscular, subcutaneous, ocular, dermal and the like. A dosage form may be packaged as tablet, gel, aerosol, fluid, particulate, capsule, powder, film, or a coating. A dosage form may also be delivered via a stent or other invasive device such as an implant, or via a pump or a patch. In another embodiment, glucagon analogs are lyophilized. In another embodiment, glucagon analogs are in solution. In another embodiment, glucagon analogs are provided as a concentrate accompanied with an appropriate dilution solution and instruction. In another embodiment, glucagon analogs are in powdered form. In another embodiment, glucagon analogs are provided as gel or in other viscous material such as polyethylene glycol. In another embodiment, glucagon analogs are provided in a micelle such as a liposome.

Glucagon Analog Kit

In one aspect, a glucagon analog described herein can be provided as a kit. In another embodiment, a kit comprises amino acids encoding a glucagon analog, a vector, a host organism, and an instruction manual. In another embodiment, a kit comprises amino acids encoding a glucagon analog, a vector, a host organism, a Ni+ column, imidazole, and an instruction manual. In another embodiment, a kit comprises an instruction manual describing methods and compositions disclosed herein. In another embodiment, a kit comprises a glucagon analog and a medical device for delivery of the glucagon analog to a patient in need thereof.

EXAMPLES

The invention is further illustrated by the following non-limiting examples.

Example 1

Building and Screening a Library of Glucagon Analogs Optimized for Thermodynamic and Chemical Stability This example describes building and screening a library of glucagon analogs. With 18 amino acids (n) (excluding Cys and Asn) being substituted in random order at 6 (r) positions from residue 22 to 27 there is an estimated $18^6(n^r)$ or 34,012,224 possible glucagon sequences.

A computational directed sequence search based upon amyloidegenic properties was used, combined with a sparse matrix method for selection of sequences to be produced and tested.

Figure 2A:
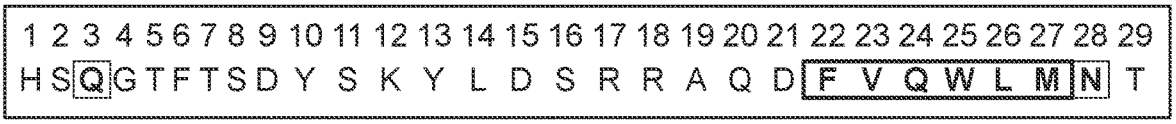
FIG. 2A shows the sequence of glucagon with calculated fibrillation sequence highlighted in dark gray and Gln3 and Asn28 highlighted in light gray. Figure discloses SEQ ID NO: 20.
Figure 2B:
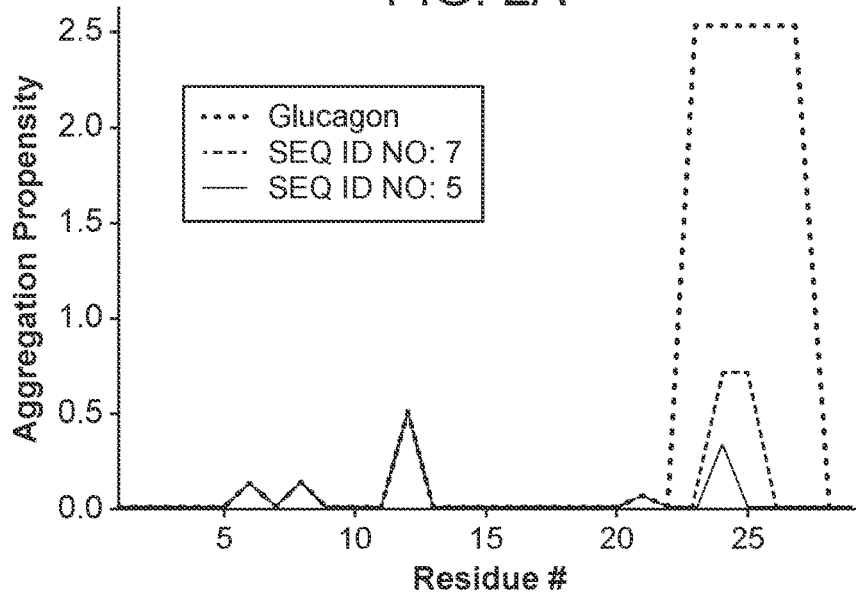
FIG. 2B shows the calculated amyloidogenic regions of glucagon (dots) and two different analogs (dashed line and solid line).
Figure 2C:
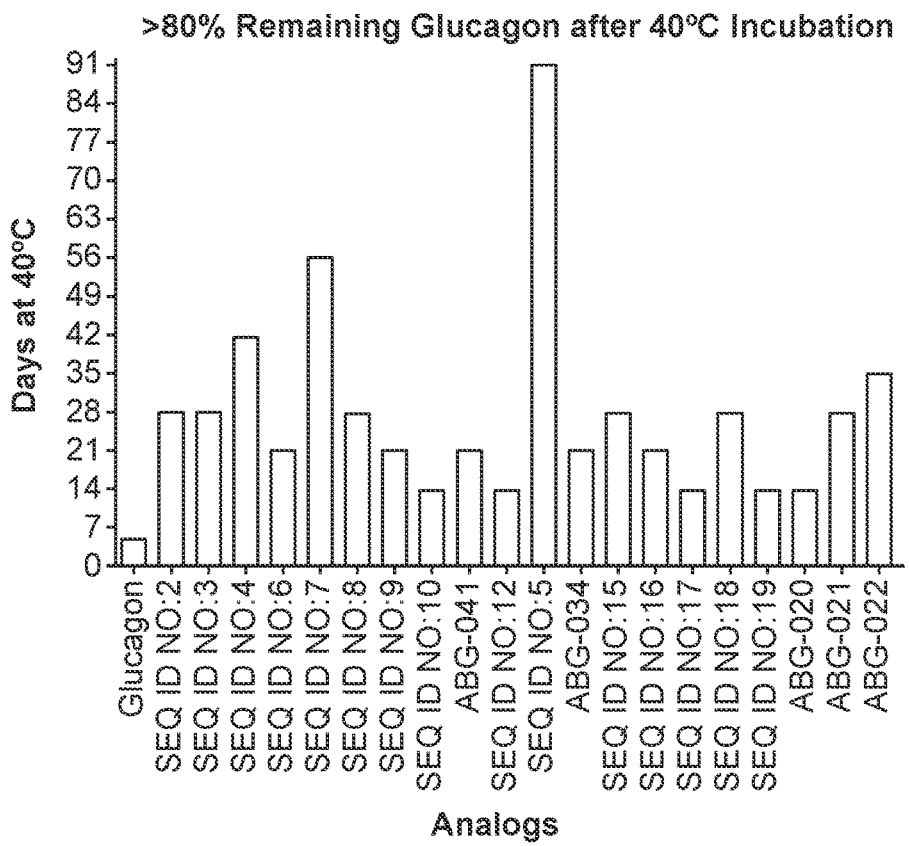
FIG. 2C shows the HPLC solution stability testing at 40° C. in PBS of a small set of predicted non-amyloidogenic glucagon analogs produced at AmideBio and compared to native glucagon.

The strategy for producing solution stable glucagon analogs is based upon the calculated fibrillation propensity of residues 22-27 in native glucagon, FIG. 2A. Using several computational tools to predict aggregation and amyloid formation a library of glucagon analogs was created.

Figure 3:
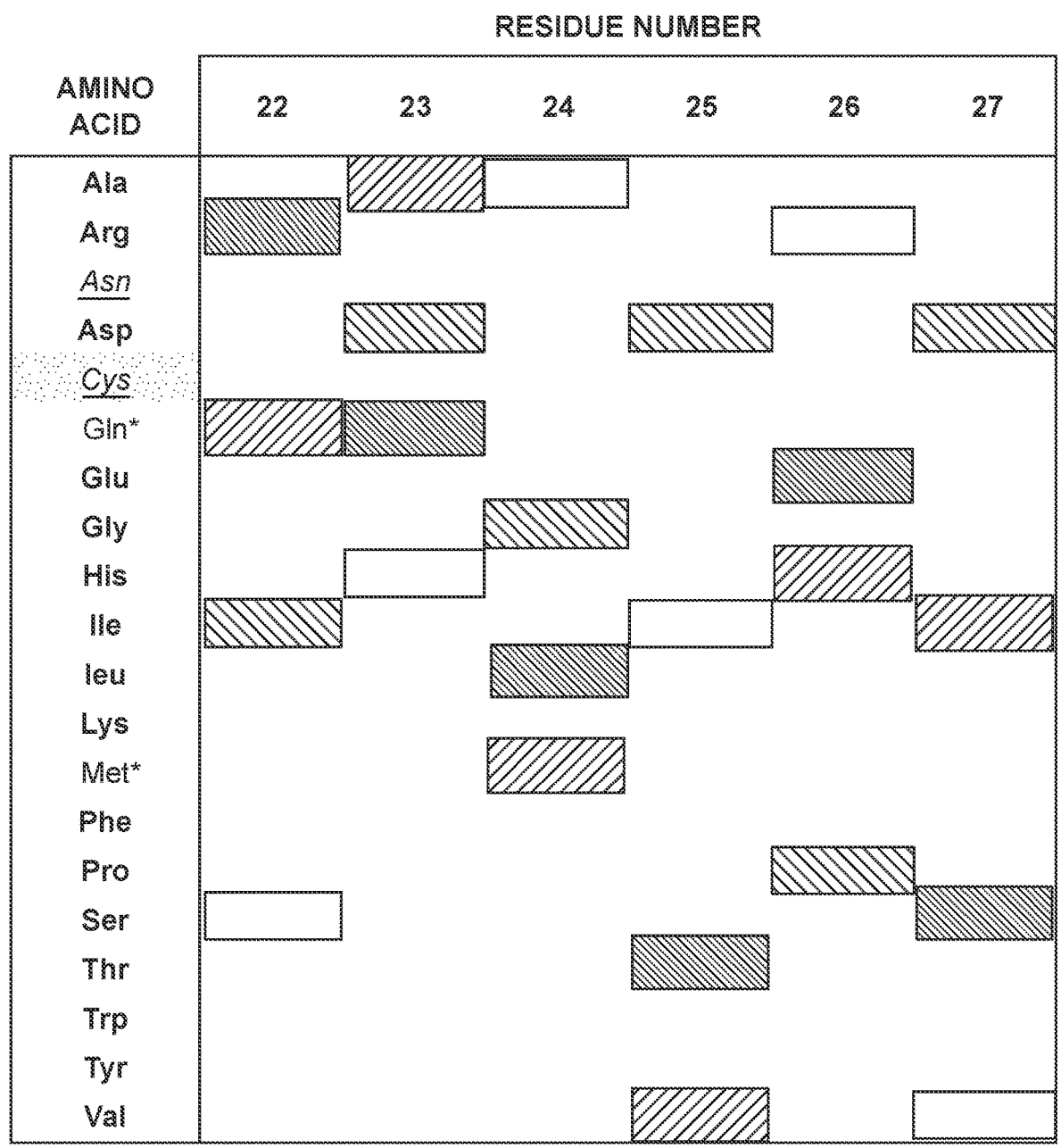
FIG. 3 shows a sparse matrix screen of substitutions within the calculated amyloidogenic region of glucagon. Each different type of box represents a single glucagon analog. The amino acids such Asn and Cys are excluded because of potential for deamidation and disulfide bond formation respectively. Gln and Met are less subject to chemical degradation or modification, i.e., oxidation.
Figure 4B:
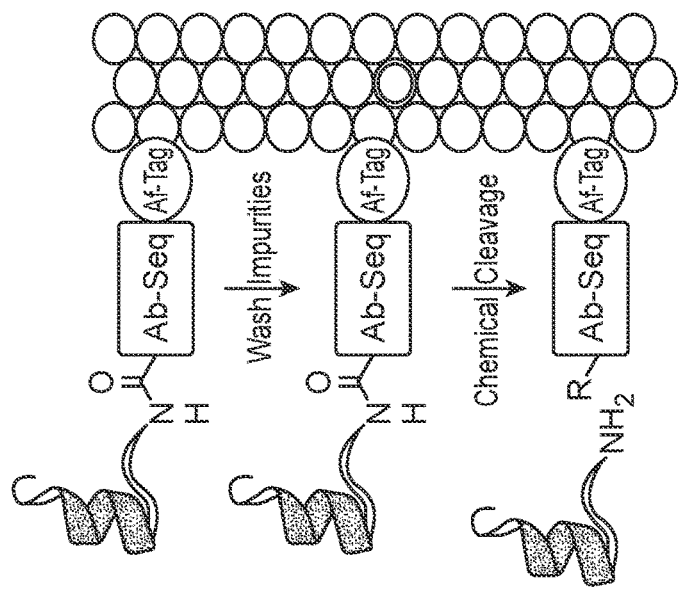
FIG. 4B shows a schematic of the on column purification method using proprietary chemical cleavage to achieve high purity (>99%) peptides.
Figure 4A:
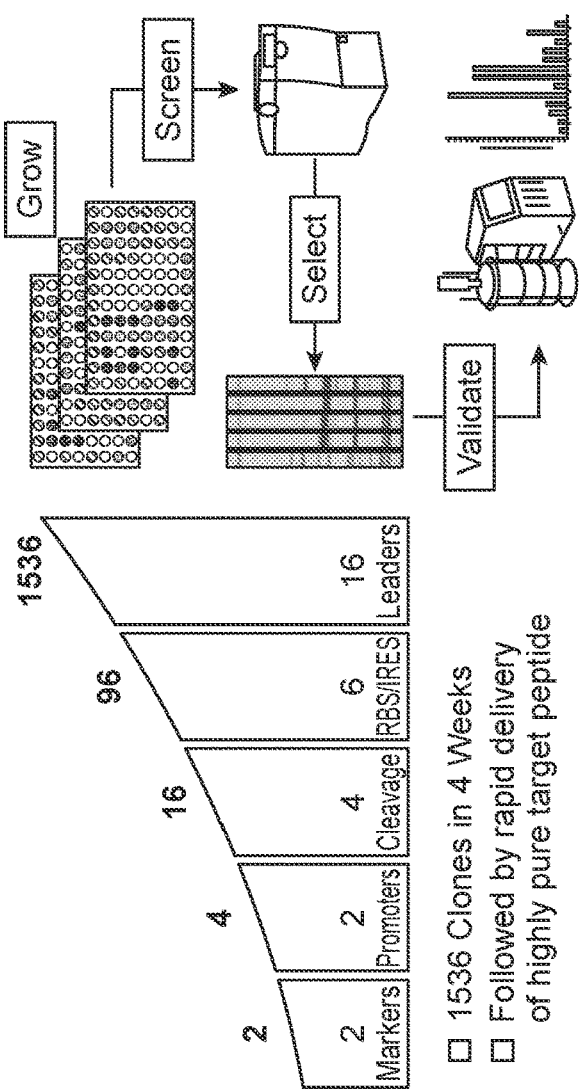
FIG. 4A shows a schematic of low cost peptide production platform combining recombinant and chemical methods for rapid SAR of complex or difficult to manufacture peptides. The process implements a library of expression vectors opimized for bacterial or yeast expression combined with an on column chemical cleavage process which provides a highly orthogonal platform enabligh the rapid high purity production of a variety of peptides and proteins for drug discovery.
Figure 4C:
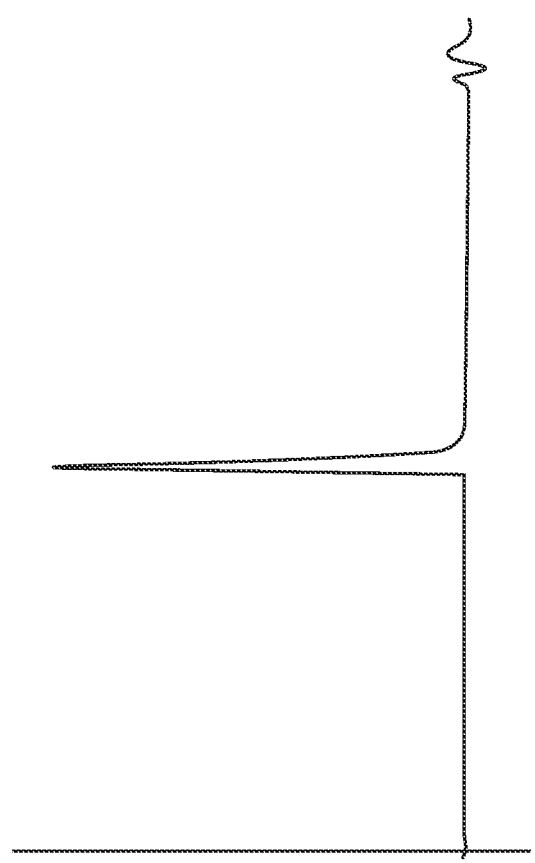
FIG. 4C shows an HPLC chromatogram of peptide following the purification process demonstrating the high purity achieved with this method.
Figure 4D:
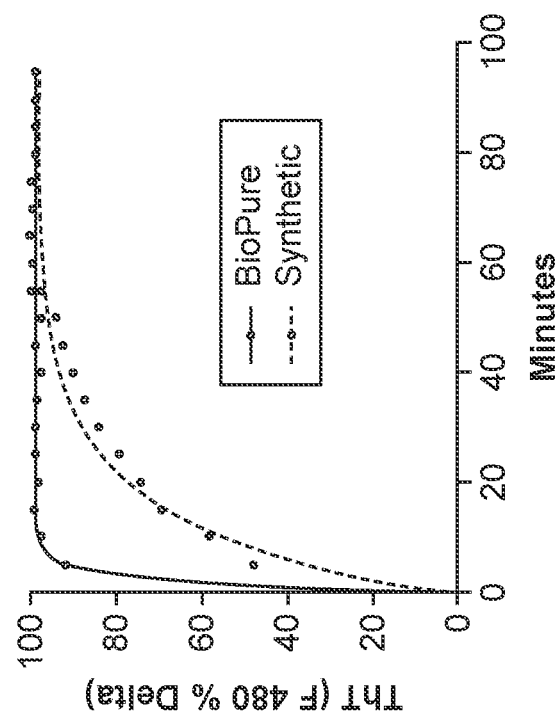
FIG. 4D shows a comparison of the aggregation rates of synthetic amyloid peptide (bottom) versus material made using AmideBio's technology platform (top). The impurities in the synthetic material dramatically alter the aggregation rates as measured using the Th-T fluorescence method.

A sparse matrix sampling approach was implemented, FIG. 3, to select members for actual production. The initial matrix was determined using the following two initial rules: eliminate sequences containing Asn, Gln, Cys or Met and eliminate sequences with a calculated aggregation propensity greater than 1.0, see FIG. 2B.

The subsequent set of sequences was then arranged in a matrix from low to high isoelectric point on the first axis and aggregation propensity on the other axis. A random sample of 40 analogs was chosen for production in subsequent biophysical testing.

Example 2

Production of Glucagon Analogs

This example describes the production of glucagon analogs. E. coli cells were transformed with an expression vector to initiate the synthesis of a glucagon analog peptide with 1 mM IPTG (GoldBio) for the production of glucagon analogs. Plated cells were incubated overnight at 37° C. and then one colony from this plate was grown up overnight in a starter culture of 8 mL of Luria broth+kanamycin. The following morning, the starter culture was inoculated into 1 L of Luria broth+kanamycin and grown to an optical density (OD) of 2.0. At this point, the cells were induced with 1 mM IPTG (GoldBio) to initiate the synthesis of glucagon analogs.

To optimize the amount of glucagon analog production in the bacteria, samples of the 1 L inoculation were taken prior to inducing the bacteria, and then 2, 4, 6, and 16 hours (overnight growth) after induction. An acrylamide gel was used to analyze the samples and select the optimal induction time.

Following induction of glucagon analog production in E. coli, lysis buffer containing 50 mM Tris pH 8.0, 150 mM NaCl, 1 mM EDTA, and 1% Triton X-100 was added before lysing the cells. Insoluble inclusion bodies were collected using washing and centrifugation. Three different wash buffers containing varying concentrations of Tris pH 8.0, NaCl, and Triton X100 were used. Once washed clean of the remaining cellular components, the insoluble inclusion bodies were solubilized in a buffer containing 8M urea, 0.193M Ethanoloamine and 2.5 mM DTT. The 8M urea served as a chaotropic agent in solubilizing protein.

Media collected from un-induced and induced bacteria, the cell lysate produced from high output sonication, and the supernatant from each washing step during the inclusion body preparation were run on an acrylamide gel. The gel was stained with Coomassie Blue reagent, and the appearance of a band at the appropriate molecular weight provided evidence for inclusion body synthesis resulting from induction. Exemplary data showed the stages of inclusion body preparation by gel electrophoresis of cells lysed with high-power sonication and washed with a series of buffers containing different concentrations of Tris, NaCl, PMSF, Triton-X100, and urea. The disappearance of the band during successive steps and reappearance of the band upon solubilizing the inclusion bodies indicated that inclusion bodies were properly prepared. Accordingly, a lane containing cell lysate was almost entirely blue because as the cells were ruptured, and relatively large quantities of various proteins were extracted. As the lysate was washed repeatedly of impurities, the lanes became clearer.

The concentration of protein in solubilized inclusion bodies was determined via a Bradford Assay. A series of NCS cleavage reactions were run to determine the optimal conditions for tryptophanyl peptide bond cleavage. Three concentrations of NCS purchased from TCI America (equimolar, 3×, and 6×) were allowed to react with glucagon analogs for varying amounts of time (0, 15, and 30 minutes) before they were quenched with excess N-acetylmethionine (Sigma). Cleavage was monitored by running the cleavage product on an acrylamide gel and observing a band at the appropriate molecular weight.

SP Sepharose High Performance Chromatography resin purchased from GE was equilibrated with refolding buffer. Next, the resin was charged with refolded fusion protein and the flow through was collected. The column was then washed with five column volumes of 20 mM Tris buffer, pH8.0 to remove impurities, urea and flow through. Afterwards, NCS was loaded and flowed through the column. The column was then washed with 20 mM Tris buffer, pH7.5 to elute remaining protein of interest and the flow through was collected. Cells are induced to initiate the synthesis of glucagon analog peptides with 1 mM IPTG (Invitrogen) and 0.2% L-arabinose (Calbiotech) as follows. Plated cells were incubated overnight at 37° C. and then one colony from this plate was grown up overnight in a starter culture of 8 mL of Luria broth+ampicillin. The following morning, the starter culture was inoculated into 1 L of Luria broth+ampicillin and grown to an optical density (OD) of 0.5. At this point, the cells were induced with 1 mM IPTG (Invitrogen) and 0.2% L-arabinose (Calbiotech) to initiate the synthesis of glucagon analog peptides.

To optimize the amount of glucagon analog peptide production in the bacteria, samples of the 1 L inoculation were taken prior to inducing the bacteria, and then 2, 4, 6, and 16 hours (overnight growth) after induction. An acrylamide gel was used to analyze the samples.

Eight hours after induction, the cells were re-induced with the same concentrations of IPTG and L-arabinose as well as 100 mg of ampicillin to prevent the growth of any new strains of E. coli.

Example 3

Agitation ThT-Assay of the Peptides Produced to Select Fibrillation Resistant Variants This example describes an agitation ThT-assay that is used to select for fibrillation resistant glucagon analog variants. The glucagon analog variants produced are screened for fibrillation tendency using an agitation Th-T assay at pH values of 6.0, 6.5, 7.0, 7.5 and 8.0 at 40° C. with native glucagon as a control. This is done rapidly and with relatively high throughput, and identifies an optimal pH range for subsequent studies. Each assay requires only micrograms of material and is done in a 96 well plate format with a plate reader with the agitation controlled by the plate reader. Consequently less than a milligram of any given glucagon analog is required to complete this assay.

In addition, this method has previously been utilized for comparing recombinant amyloid peptides produced using the AmideBio technology platform, FIG. 4, demonstrating this method is able to perform this assay as well as the importance of peptide purity in these assays.

Example 4

Agitation Assay Using Quantitative HPLC Analysis

This example describes quantitative HPLC analysis of glucagon analogs. Quantitative HPLC is used to determine the extent of glucagon loss upon incubation. Samples are agitated and maintained at 40° C. Sample quantification is performed using both an internal standard of cresol as well as a comparator sample maintained at 4° C.

Example 5

Agitation Assay Using Transmission Electron Microscopy

This example describes transmission electron microscopy of glucagon analogs. As a further test to monitor the nature of aggregation a negative stain (1% uranyl acetate) electron microscopy is used to visually inspect the nature of any aggregation. Data is digitally collected on a Gatan Ultrascan CCD camera mounted on a FEI/Phillips CM120 at the EM facilities at CU Boulder. Images will be collected at 4800× as 1K×1K pixel images. The aggregation of glucagon analogs is assessed.

Example 6

LC-MS to Select Deamidation Resistant Variants

This example describes LC-MS/MS of glucagon analogs to select for deamidation resistant variants. LC-MS is performed to select deamidation resistant glucagon analog variants.

Microgram samples of glucagon analog variants are stored in buffers at pH 6.0 and 8.0 at 40° C. for 30 days and analyzed by LC-MS/MS to determine the extent of deamidation (+1 mass) or other chemical modifications at the two pH extremes.

Figure 5:
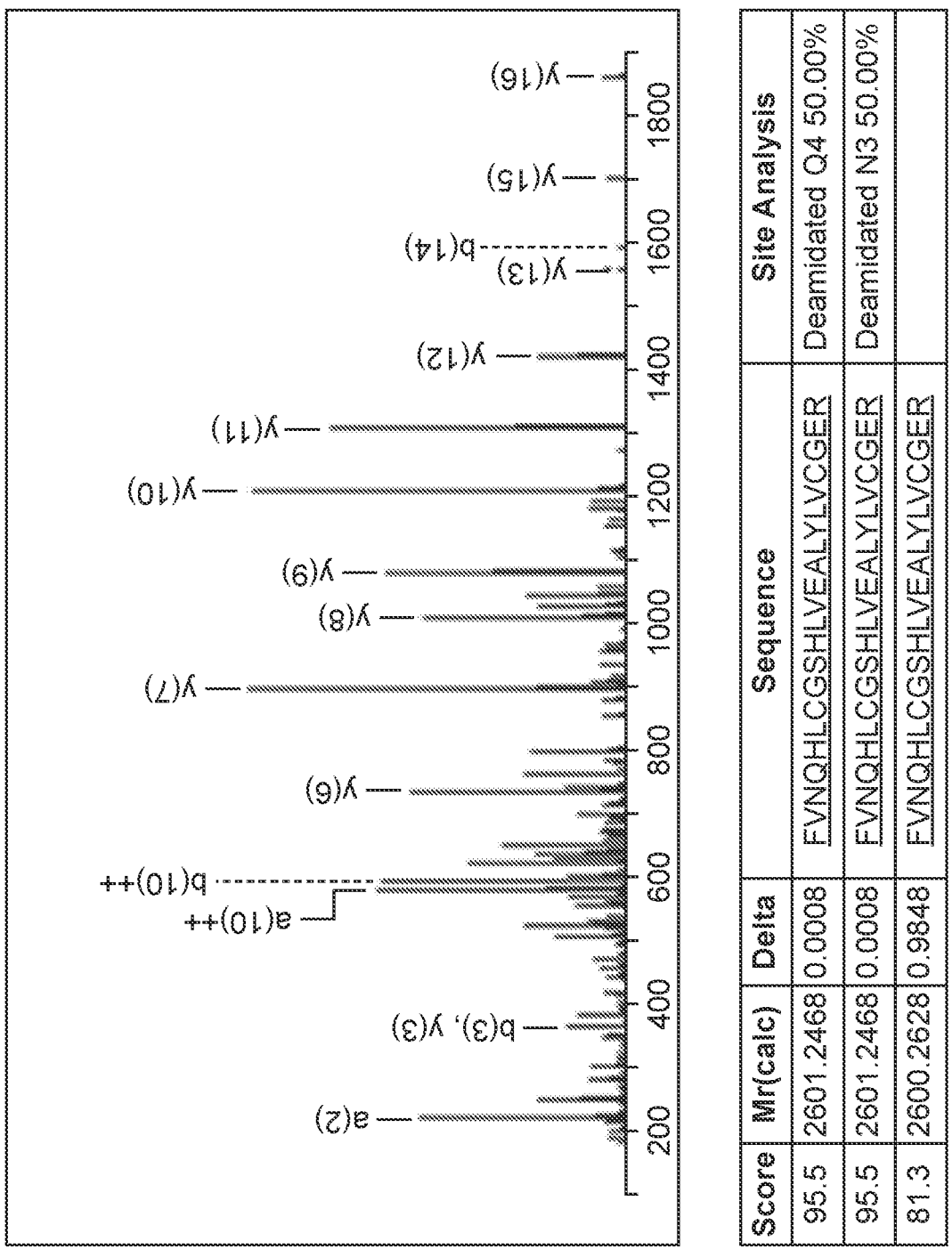
FIG. 5 shows LC-MS/MS raw spectral data and peak assignment for an insulin fragment (top) demonstrating the detection of deamidation within the peptide fragment upon incubation at 40° C. for 30 days, and mass assignment (bottom) demonstrating the mass equivalence of Q4 or N3 deamidation. Figure discloses SEQ ID NOs: 30, 30 and 30, respectively, in order of appearance.

LC-MS/MS was previously employed to quantify deamidation rates of single chain insulin molecules, FIG. 5, demonstrating detection and quantification of deamidation as well as other modifications such as oxidation. Deamidation of glucagon is identified similarly.

Example 7

In Vitro Assay Profiling for Glucagon Activity Using a Glucagon Receptor Fluorescent Imaging Plate Reader (FLIPR) Assay This example describes in vitro assay profiling for glucagon activity using an agonist FLIPR assay and an antagonist FLIPR assay. Analogs demonstrating enhanced resistance to fibrillation and chemical degradation were characterized in a $Ca^{++}$ FLIPR assay. Both agonist and antagonist activity were tested by this assay to ensure that the glucagon analogs have suitable activation of the glucagon receptor without any residual antagonist properties.

In the agonist FLIPR assay, analogs were plated in triplicate for each concentration assayed. Reference agonist (glucagon) was prepared in a similar manner to serve as assay control included at $E_{max}$ (the concentration where the reference agonist elicited a maximal response).

Figure 6B:
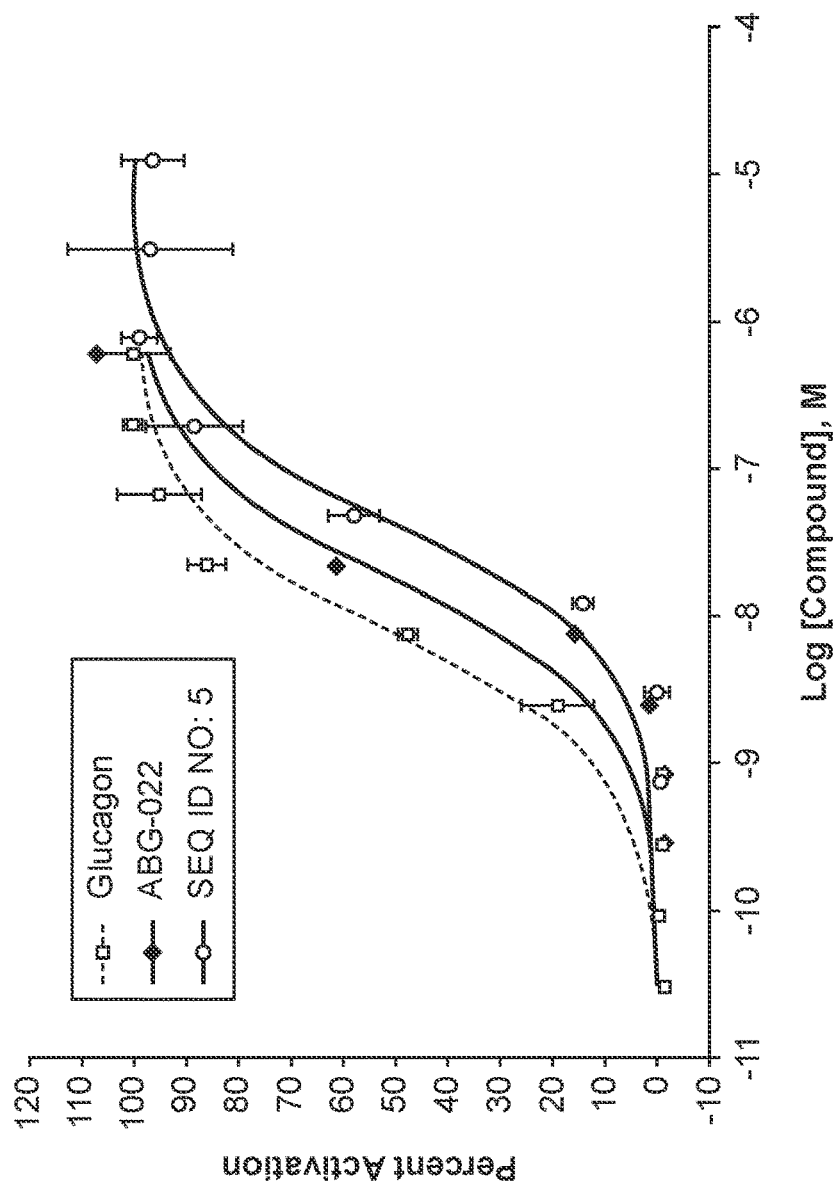
FIG. 6B shows a FLIPR assay comparing native glucagon activity to the AmideBio analogs GLUC-22 and GLUC-45. The calculated EC50 of the analog was 5 times higher than native glucagon.
Figure 6A:
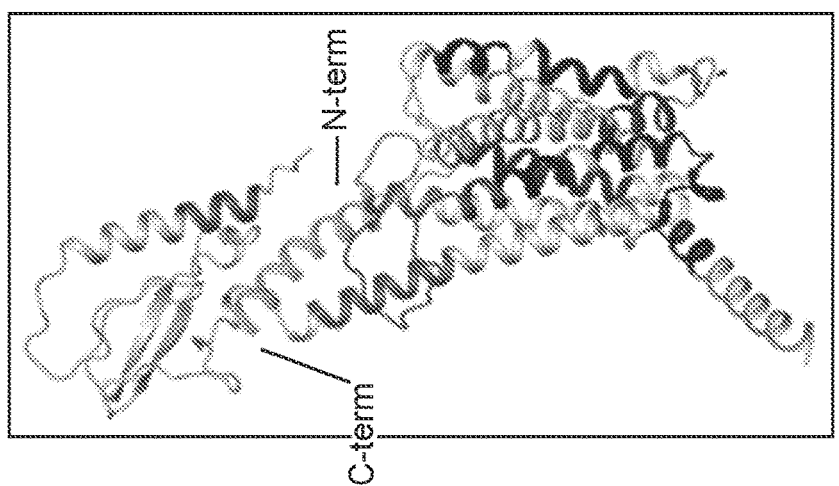
FIG. 6A: shows a 3D structure of glucagon receptor (left) (Siu et al. 2013) with glucagon modelled into the receptor structure, and the N-terminus of glucagon primarily interacts with the 7TM integral membrane domain and the C-terminus has a minor interaction with the extracellular domain of the receptor.

Assay data was collected on a FLIPRTETRA instrument where the analogs, vehicle controls, and reference glucagon were added to the assay plate after a fluorescence/luminescence baseline was established. The assay time was typically 180 seconds and the normalized response for each dose was used to calculate a binding curve as in FIG. 6. Glucagon analogs that had at least 10% of native glucagon activity were chosen for further testing.

In the antagonist FLIPR assay, EC80 potency values determined during the agonist assay were used and all pre-incubated glucagon analog wells were challenged with an EC80 concentration of native glucagon after a fluorescence/luminescence baseline was established. This was used to ensure that none of the active analogs have any residual unexpected antagonist activity which could complicate the use of such compounds for treating CH as well as other indications.

Example 8

Treatment of Type I Diabetes Using a Glucagon Analog

This example describes treatment of Type I Diabetes using a glucagon analog. A subject is determined to have hypoglycemia. An effective amount of a glucagon analog is administered to the subject via intravenous injection.

Example 9

Treatment of Congenital Hyperinsulinism Using a Glucagon Analog

This example describes treatment of congenital hyperinsulinism using a glucagon analog. A subject is diagnosed with Congenital Hyperinsulinism (CH). A glucagon analog is administered to the patient via a pump. A closed loop pump system is used by the subject to deliver the glucagon analog.

While preferred embodiments of the present invention have been shown and described herein, it will be apparent to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

What is claimed:

1. A composition of comprising a glucagon analog, wherein the glucagon analog comprises SEQ ID NO: 16.

2. A method for producing a glucagon analog, the method comprising:
   expressing a heterologous fusion peptide in a genetically modified cell, the heterologous fusion peptide comprising:
   an expression tag comprising an amino acid sequence having at least 80% sequence identity to SEQ ID NO: 21 or a fragment thereof;
   a cleavage tag comprising a Trp amino acid; and
   a glucagon analog comprising SEQ ID NO: 16, wherein the glucagon analog consists of amino acids, and the glucagon analog has a decreased computed aggregation score compared to native glucagon and decreased experimental aggregation after a time period of at least 7 days in solution; and
   cleaving the heterologous fusion peptide to release the glucagon analog from the heterologous fusion peptide, thereby producing the glucagon analog.

3. The method of claim 2, further comprising binding the heterologous fusion peptide to an affinity material via an affinity tag.

4. The method of claim 3, wherein subsequent to binding the heterologous fusion peptide to the affinity material, the method further comprises washing the affinity material to remove unbound material.

5. The method of claim 3, wherein cleaving the heterologous fusion peptide to release the glucagon analog occurs while the heterologous fusion peptide is bound to the affinity material via the affinity tag.

6. The method of claim 3, wherein subsequent to binding the heterologous fusion peptide to the affinity material, the method further comprises subjecting the heterologous fusion peptide to conditions sufficient to fold the target peptide.

* * * * *